United States Patent
Van Egmond et al.

(10) Patent No.: US 7,074,971 B2
(45) Date of Patent: Jul. 11, 2006

(54) RECOVERY OF ETHYLENE AND PROPYLENE FROM A METHANOL TO OLEFIN REACTION SYSTEM

(75) Inventors: Cor F. Van Egmond, Pasadena, TX (US); Jeffrey L. Brinen, League City, TX (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 97 days.

(21) Appl. No.: 10/383,204

(22) Filed: Mar. 6, 2003

(65) Prior Publication Data

US 2004/0176646 A1 Sep. 9, 2004

(51) Int. Cl.
*C07C 41/42* (2006.01)

(52) U.S. Cl. ............... 568/699; 585/809; 585/259; 585/264; 585/250; 585/639; 585/500; 203/38; 203/39; 203/75; 203/76; 203/77

(58) Field of Classification Search .......... 585/639, 585/809, 259, 250, 264, 500; 203/38, 39, 203/75, 76, 77; 568/699; 526/77
See application file for complete search history.

(56) References Cited

U.S. PATENT DOCUMENTS

| | | | | |
|---|---|---|---|---|
| 2,728,754 A * | 12/1955 | Evering et al. | ............... | 526/69 |
| 4,474,647 A | 10/1984 | Asselineau et al. | ........... | 203/49 |
| 4,587,373 A | 5/1986 | Hsia | ............ | 585/639 |
| 4,898,717 A | 2/1990 | Hsia et al. | .................. | 422/190 |
| 5,122,236 A | 6/1992 | Smith, Jr. et al. | ............. | 203/43 |
| 5,336,841 A | 8/1994 | Adams | ........................ | 203/28 |
| 5,609,734 A | 3/1997 | Streicher et al. | .............. | 203/39 |
| 5,723,686 A | 3/1998 | Patton et al. | ................ | 568/697 |
| 5,811,621 A | 9/1998 | van Dijk | ..................... | 585/639 |
| 5,908,964 A | 6/1999 | Koskinen et al. | ............ | 568/697 |
| 6,121,504 A | 9/2000 | Kuechler et al. | ............ | 585/640 |
| 6,303,841 B1 * | 10/2001 | Senetar et al. | .............. | 585/639 |
| 6,444,869 B1 | 9/2002 | Senetar et al. | .............. | 585/809 |
| 2003/0004386 A1 | 1/2003 | Lattner et al. | .............. | 585/804 |
| 2003/0125597 A1 * | 7/2003 | Cheng et al. | ................ | 585/639 |
| 2003/0199721 A1 * | 10/2003 | Ding et al. | ................. | 585/807 |
| 2003/0199724 A1 * | 10/2003 | Van Egmond et al. | ...... | 585/899 |
| 2004/0039239 A1 * | 2/2004 | Shutt | .......................... | 585/639 |
| 2004/0122272 A1 * | 6/2004 | Van Egmond et al. | ...... | 585/634 |

FOREIGN PATENT DOCUMENTS

| WO | 03/020673 | 3/2003 |
|---|---|---|
| WO | 03/020678 | 3/2003 |

OTHER PUBLICATIONS

U.S. Appl. No. 10/292,232, filed Nov. 12, 2002, Ding et al.
U.S. Appl. No. 10/124,859, filed Apr. 18, 2002, Ding et al.
U.S. Appl. No. 10/125,138, filed Apr. 18, 2002, Van Egmond et al.

* cited by examiner

*Primary Examiner*—Rosalynd Keys

(57) ABSTRACT

The present invention provides new highly-efficient separation processes and systems for separating polymerization-grade ethylene and propylene from an initial effluent stream comprising ethane, ethylene, propylene, dimethyl ether, and one or more of propane, acetylene, methyl acetylene, propadiene, methane, hydrogen, carbon monoxide, carbon dioxide and C4+ components. In one embodiment, the initial effluent stream is provided from a methanol-to-olefin reaction system. It has been discovered that the best separation of these components is realized when DME is selectively removed in a first separation step, followed by separation of the remaining components in additional separation steps.

94 Claims, 3 Drawing Sheets

RECOVERY OF ETHYLENE AND PROPYLENE FROM A METHANOL TO OLEFIN REACTION SYSTEM

FIELD OF THE INVENTION

The present invention relates to ethylene and propylene recovery systems. More particularly, the present invention relates to recovering ethylene and propylene from a mixed effluent stream comprising one or more of methane, dimethyl ether, ethane, ethylene, propane, propylene and acetylene.

BACKGROUND OF THE INVENTION

Light olefins such as ethylene and propylene are important commodity petrochemicals useful in a variety of processes for making plastics and other chemical compounds. Ethylene is used to make various polyethylene plastics, and in making other chemicals such as vinyl chloride, ethylene oxide, ethylbenzene and alcohol. Propylene is used to make various polypropylene plastics, and in making other chemicals such as acrylonitrile and propylene oxide. The petrochemical industry has known for some time that oxygenates, especially alcohols, are convertible into light olefins. The preferred conversion process is generally referred to as an oxygenate-to-olefin (OTO) or specifically to methanol-to-olefins (MTO) process, where methanol is converted to primarily ethylene and/or propylene in the presence of a molecular sieve catalyst.

Various byproducts are produced in the MTO reaction process. These byproducts may include components that are heavier than propane and propylene, such as $C_4+$ components (olefinic and aliphatic) as well as multiply unsaturated components such as acetylene, methyl acetylene and propadiene. Oxygenate compounds such as alcohols, aldehydes, ketones, esters, acids and ethers in the $C_1$ to $C_6$ range as well as trace quantities of aromatic compounds may also be formed in MTO reactors or in MTO effluent processing. Additionally, a small amount of oxygenate from the feedstock, e.g., methanol and/or dimethyl ether ("DME"), can pass through the MTO reactor with the product effluent without being converted to desired product. As a result of oxygenate synthesis and/or oxygenate "pass through" in an MTO reactor system, the effluent from an MTO reactor can contain undesirably high concentrations of oxygenate compounds. These oxygenates, particularly light oxygenates, are in amounts that would make the ethylene and propylene off-specification for their preferred dispositions, e.g., polymerization.

Various processing schemes have been developed for separating one or more of these components from non-MTO effluent streams. For example, U.S. Pat. No. 5,336,841 to Adams is directed to a process for removing oxygenates from a C4 raffinate stream from an MTBE plant. A back-cracking catalyst is placed into the bottom of an oxygenate removal column, which converts any MTBE or tertiary butyl alcohol contained therein back to their original components of isobutene and methanol or water. The raffinate stream is first subjected to a water wash to remove the gross amounts of methanol and DME.

U.S. Pat. No. 5,122,236 to Smith et al. is directed to a process for removing DME and methanol impurities from a $C_4$ hydrocarbon stream without substantial loss of $C_4$ hydrocarbons by fractionating a $C_4$ hydrocarbon stream containing DME and methanol at low levels, e.g., less than 5 weight percent, to produce an overhead of about 20 to 40 volume percent of the $C_4$ stream, condensing the overhead, contacting the condensed overhead with about 1 to 5 volumes of water, thereby removing a portion of the DME and methanol from the $C_4$ stream, returning substantially all of the $C_4$ stream, except the small amount solubilized in the water, to the fractionation and flashing the solubilized DME and hydrocarbons from the water.

U.S. patent application Ser. No. 10/292,232 filed Nov. 12, 2002, the entirety of which is incorporated herein by reference, is directed to a particularly desirable process for recovering $C_4$ olefins from a product stream comprising $C_4$ olefins, dimethyl ether and $C_5+$ hydrocarbons. The process includes first separating out $C_5+$ hydrocarbons and coboiling oxygenates, if any, from a stream comprising $C_5+$ hydrocarbons, DME and $C_4$ hydrocarbons. By first separating out the $C_5+$ hydrocarbons and coboiling oxygenates, a more efficient separation of DME from $C_4$ olefins by water wash is obtainable.

Although a variety of processes have been described for separating $C_4+$ components from $C_3-$ components, separation schemes for efficiently recovering ethylene and propylene from other $C_3-$ components in a mixed effluent stream have not been widely described and have heretofore proven generally inefficient. Specifically, recovery of ethylene and propylene from lighter less desirable components, particularly from DME, has proven inefficient when the effluent stream contains a mixture of methane, DME, ethane, ethylene, propane and propylene. Thus, a need exists for efficiently separating ethylene and propylene from an MTO reaction system effluent stream containing these $C_3-$ components, or from a similar effluent stream derived from another reaction process.

SUMMARY OF THE INVENTION

The present invention provides novel process flow schemes which produce on-spec ethylene and propylene product streams for polymer feedstock disposition from an initial effluent stream comprising dimethyl ether (DME), ethane, ethylene, propylene, and, optionally, one or more of propane, acetylene, methyl acetylene, propadiene, methane, hydrogen, carbon monoxide, carbon dioxide and C4+ components. The process flow schemes are highly efficient in removing DME and minimizing equipment count. It has been discovered that the best separation of these components is realized when DME is selectively removed, at least partially, in a first separation step, followed by separation of the remaining components in additional separation steps. Moreover, the process flow schemes ensure thorough acetylene conversion by integrating one or more hydrogenation converters therein.

In one embodiment, the present invention provides a process for separating components from an olefin-containing effluent stream. The process includes providing the effluent stream, wherein the effluent stream contains ethane, ethylene, propylene, and dimethyl ether. The effluent stream is separated in a first separation unit into a first fraction and a second fraction, wherein the first fraction contains a majority of the ethane, ethylene and propylene present in the effluent stream, and wherein the second fraction contains a majority of the dimethyl ether present in the effluent stream. At least a portion of the first fraction is separated into a third fraction and a fourth fraction, wherein the third fraction contains a majority of the ethylene and ethane present in the at least a portion of the first fraction, and wherein the fourth fraction contains a majority of the propylene present in the at least a portion of the first fraction.

In another embodiment, the present invention provides a process for separating components from an olefin-containing effluent stream. In this embodiment, the process includes providing the effluent stream, wherein the effluent stream contains methane, ethane, ethylene, propane, propylene, and dimethyl ether. The effluent stream is separated in a first separation unit into a first fraction and a second fraction, wherein the first fraction contains a majority of the methane, ethane, ethylene, propane and propylene present in the effluent stream, and wherein the second fraction contains a majority of the dimethyl ether present in the effluent stream. At least a portion of the first fraction is separated into a third fraction and a fourth fraction, wherein the third fraction contains a majority of the methane that was present in the at least a portion of the first fraction, and wherein the fourth fraction contains a majority of the ethylene, ethane, propylene and propane that was present in the at least a portion of the first fraction.

In one embodiment, the present invention is a process for selectively hydrogenating acetylene. The process comprises providing an effluent stream containing methane, acetylene, ethylene, ethane, propylene, propane and dimethyl ether. The effluent stream is separated in a first separation unit into a first fraction and a second fraction, wherein the first fraction contains a first portion of the propane and a majority of the methane, ethane, ethylene and propylene present in the effluent stream, and wherein the second fraction contains a second portion of the propane and a majority of the dimethyl ether present in the effluent stream. At least a portion of the first fraction is separated into a third fraction and a fourth fraction, wherein the third fraction contains a majority of the methane, ethylene and ethane present in the at least a portion of the first fraction, and wherein the fourth fraction contains a majority of the propylene and propane present in the at least a portion of the first fraction. At least a portion of the third fraction is separated into a fifth fraction and a sixth fraction, wherein the fifth fraction contains a majority of the methane present in the at least a portion of the third fraction, and wherein the sixth fraction contains a majority of the ethylene and ethane present in the at least a portion of the third fraction. At least a portion of the sixth fraction is separated into a seventh fraction and an eighth fraction, wherein the seventh fraction contains a majority of the ethylene present in the at least a portion of the sixth fraction, and wherein the eighth fraction contains a majority of the ethane present in the at least a portion of the sixth fraction. Acetylene in an acetylene-containing stream contacts hydrogen and carbon monoxide in a conversion unit under conditions effective to at least partially hydrogenate at least a portion of the acetylene in the acetylene-containing stream. The acetylene-containing stream is selected from the group consisting of the first fraction, the third fraction, the sixth fraction and the seventh fraction.

Another embodiment of the present invention provides for efficiently removing DME from an initial effluent stream in a plurality of DME removal steps. This inventive process includes the step of providing the effluent stream, wherein the effluent stream contains ethane, ethylene, dimethyl ether, and propylene. The effluent stream is separated into a first fraction and a second fraction, wherein the first fraction contains at least 5, 10, 20 or 60 weight percent of the dimethyl ether and a majority of the ethane, ethylene and propylene that was present in the effluent stream. The second fraction contains at least 5, 10, 20 or 30 weight percent of the dimethyl ether and a majority of the C4+ components that were present in the effluent stream. At least a portion of the first fraction is separated into a third fraction and a fourth fraction, wherein the fourth fraction contains a majority of the dimethyl ether present in the at least a portion of the first fraction.

BRIEF DESCRIPTION OF THE DRAWINGS

This invention will be better understood by reference to the Detailed Description of the Invention when taken together with the attached drawings, wherein.

DETAILED DESCRIPTION OF THE INVENTION

Introduction

Figure 1:
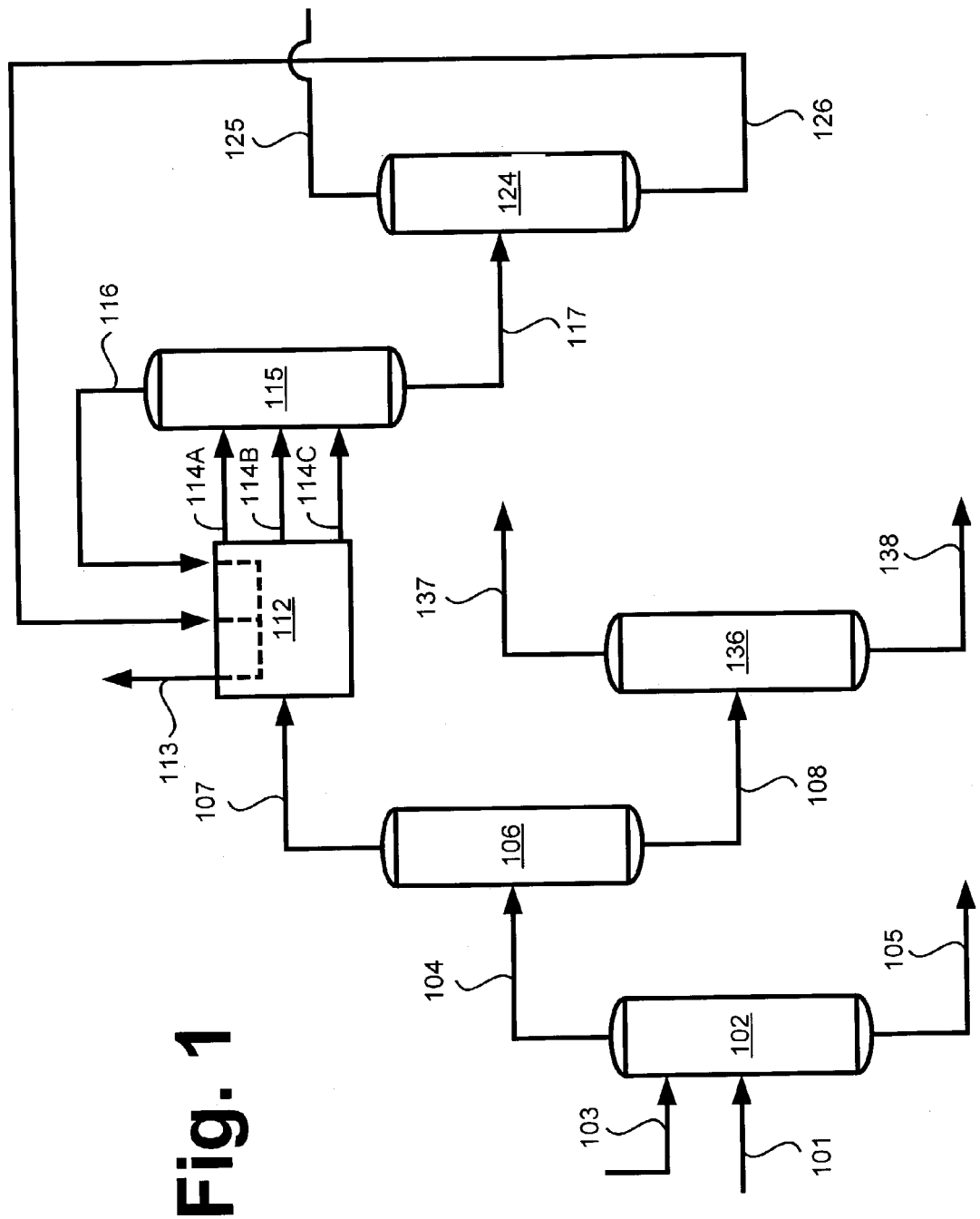
FIG. 1 illustrates a separation scheme according to one embodiment of the present invention.

The present invention provides new highly-efficient separation processes and systems for separating polymerization-grade ethylene and propylene from an "initial effluent stream," defined herein as a stream containing dimethyl ether (DME), ethane, ethylene and propylene. Additionally, the initial effluent stream optionally includes one or more of propane, acetylene, methyl acetylene, propadiene, methane, hydrogen, carbon monoxide, carbon dioxide and C4+ components (aliphatic and/or olefinic). In one particularly preferred embodiment, the initial effluent stream is derived from the product effluent of a methanol-to-olefin (MTO) reaction process, described in detail below. It has been discovered that the best separation of these components is realized when DME is selectively removed, at least partially, in a first separation step, followed by separation of the remaining components in additional separation steps.

The Initial Effluent Stream

The initial effluent stream may be derived from a variety of sources. For example, in one embodiment, the initial effluent stream is derived from a product effluent of a reaction selected from the group consisting of an olefin interconversion reaction, an oxygenate to olefin (OTO) reaction, an oxygenate to gasoline conversion reaction, malaeic anhydride formulation, vapor phase methanol synthesis, phthalic anhydride formulation, a Fischer Tropsch reaction, and an acrylonitrile formulation. Preferably, the initial effluent stream is derived from an effluent stream of an MTO reaction system.

The composition of the initial effluent stream will now be described. The initial effluent stream contains ethane, ethylene, propylene and DME. In one embodiment of the exemplary separation process, the initial effluent stream that is provided comprises not greater than about 50 weight percent DME, preferably not greater than about 20 weight percent DME, more preferably not greater than about 10 weight percent DME, and most preferably not greater than about 5 weight percent DME. Of course, for DME to be removed from the initial effluent stream, some measurable amount must be present. Desirably, the provided initial effluent stream will contain at least about 100 wppm DME, preferably at least about 500 wppm DME, and more preferably at least about 1,000 wppm DME. As used herein, "weight percent" is based on the total weight of all components in a specified stream.

In another embodiment of the inventive process, the initial effluent stream that is provided comprises at least about 25 weight percent ethylene. Preferably, the provided initial effluent stream comprises from about 25 weight percent ethylene to about 75 weight percent ethylene, more preferably from about 30 weight percent to about 60 weight percent, and most preferably from about 35 weight percent to about 50 weight percent propylene.

In another embodiment, the initial effluent stream that is provided also comprises at least about 20 weight percent propylene. Preferably, the provided initial effluent stream comprises from about 20 weight percent propylene to about 70 weight percent propylene, more preferably from about 25 weight percent to about 50 weight percent propylene, and most preferably from about 30 weight percent to about 40 weight percent propylene. In terms of lower range limitations, the initial effluent stream preferably comprises at least about 5 weight percent, more preferably at least about 10 weight percent, and most preferably at least about 15 weight percent propylene. In still another embodiment, the effluent stream contains from 25 to 75 weight percent propylene, based on the total weight of the effluent stream.

In another embodiment of the DME removal process, the initial effluent stream contains both ethylene and propylene. Desirably, the initial effluent stream contains at least about 50 weight percent ethylene and propylene. Preferably, the initial effluent stream contains from about 50 weight percent to about 95 weight percent ethylene and propylene, more preferably from about 55 weight percent to about 90 weight percent ethylene and propylene, and most preferably from about 60 weight percent to about 85 weight percent ethylene and propylene.

It is desirable that the provided initial effluent stream contain a relatively low concentration of ethane, preferably a lower concentration of ethane than propane. Preferably, the initial effluent stream comprises not greater than about 4 weight percent ethane, more preferably not greater than about 3 weight percent ethane, and most preferably not greater than about 2 weight percent ethane. In terms of lower range limitations, the initial effluent stream preferably comprises at least about 0.1 weight percent, more preferably at least about 0.5 weight percent, and most preferably at least about 1.0 weight percent ethane.

It is also desirable that the initial effluent stream contain a relatively low concentration of propane, if any. Preferably, the initial effluent stream comprises not greater than about 5 weight percent propane, more preferably not greater than about 4 weight percent propane, and most preferably not greater than about 3 weight percent propane. In terms of lower range limitations, the initial effluent stream optionally contains at least about 0.1 weight percent, more preferably at least about 0.5 weight percent, and most preferably at least about 1.0 weight percent propane.

The initial effluent stream also optionally contains one or more of acetylene, and C4+ components. If the initial effluent stream contains acetylene, the initial effluent stream preferably contains less than about 50 wppm, more preferably less than about 10 wppm, and most preferably less than about 1.0 wppm acetylene. In terms of lower range limitations, the initial effluent stream optionally contains at least about 0.1 wppm, more preferably at least about 0.5 wppm, and most preferably at least about 1.0 wppm acetylene. The initial effluent stream to be processed according to the present invention optionally is depleted in C4+ hydrocarbons and C4+ olefins (C4+ components, collectively). The initial effluent stream preferably contains less than about 30 weight percent, more preferably less than about 20 weight percent, and most preferably less than about 15 weight percent C4+ components. In terms of lower range limitations, the initial effluent stream optionally contains at least about 1 weight percent, more preferably at least about 5 weight percent, and most preferably at least about 10 weight percent C4+ components. The initial effluent stream also preferably contains less than about 10 weight percent, more preferably less than about 5 weight percent, and most preferably less than about 1 weight percent C4+ olefins. The initial effluent stream also preferably contains less than about 1.0 weight percent, more preferably less than about 0.5 weight percent, and most preferably less than about 0.1 weight percent C4+ hydrocarbons.

Additionally, the initial effluent stream may include a minor amount of other components such as methyl acetylene, propadiene, and light ends, e.g., methane, carbon monoxide and/or hydrogen. As used herein, "light ends" means components having a normal boiling point less than about $-166°$ F. ($-110°$ C.) and carbon dioxide. An exemplary list of light ends includes methane, carbon monoxide and hydrogen. The initial effluent stream to be processed according to the present invention preferably contains less than about 1.0 weight percent, more preferably less than about 0.5 weight percent, and most preferably less than about 0.01 weight percent light ends. The initial effluent stream preferably contains less than about 1.0 weight percent, more preferably less than about 0.5 weight percent, and most preferably less than about 0.1 weight percent methane. In terms of lower range limitations, the initial effluent stream optionally contains at least about 0.001 weight percent, more preferably at least 0.005 weight percent, and more preferably at least 0.01 weight percent light ends. The initial effluent stream optionally contains at least about 0.001 weight percent, more preferably at least 0.005 weight percent, and more preferably at least 0.01 weight percent methane. The initial effluent stream preferably contains less than about 0.01 weight percent, more preferably less than about 0.005 weight percent, and most preferably less than about 0.001 weight percent carbon monoxide. In terms of lower range limitations, the initial effluent stream optionally contains at least about 0.0001 weight percent, more preferably at least 0.0005 weight percent, and more preferably at least about 0.001 weight percent carbon monoxide.

The provided initial effluent stream can also contain some amount of water. However, it is desirable that any water present in the initial effluent stream will be at a concentration such that free water formation (i.e., formation of a separate water phase) or gas hydration does not significantly impede the separation process. Gas hydration results in the formation of a clathrate compound. Clathrate compounds are solids, and are essentially insoluble in water and hydrocarbons. Such compounds can cause significant problems in the separation process.

Thus, water that is present in the provided initial effluent stream should be at a concentration sufficiently low such that a separate water phase is not formed during the separation process. This is particularly important when a distillation column having trays is used in the inventive process, since a separate water phase formed in the trays will impede mass transfer and add extra weight to each tray. Distillation columns having packing are preferred at higher concentrations of water, since such a column will not have trays to hold up separate water phases.

It is desirable in this separation system that the provided initial effluent stream contain not greater than about 15,000 wppm water. Preferably the initial effluent stream contains not greater than about 10,000 wppm water, more preferably not greater than 5,000 wppm water, and most preferably not greater than about 1,000 wppm water.

It is not necessary in this invention that the initial effluent stream be completely dry. That is, the initial effluent stream can contain some water. The benefit of the initial effluent stream containing some amount of water is that additional and/or complex drying equipment will not be needed before separating the DME from the initial effluent stream. In the low pressure separation embodiment, described below, the initial effluent stream preferably contains at least about 10 wppm water, more preferably at least about 20 wppm water, and most preferably at least about 25 wppm water. The high pressure separation embodiment, also described below, can tolerate more water than the low pressure separation. In the high pressure separation embodiment, the initial effluent stream preferably contains at least about 10 wppm water, more preferably at least about 100 wppm water, and most preferably at least about 200 wppm water.

If the initial effluent stream contains an unacceptably high concentration of water, a sufficient amount of the water can be removed either prior to or during separation of the DME using a water absorbent. Examples of water absorbents include alcohols, amines, amides, nitrites, heterocyclic nitrogen containing compounds, or a combination of any of the preceding. Either monohydric alcohols or polyhydric alcohols can be used as the alcohol absorbent. Specific examples of absorbents include methanol, ethanol, propanol, ethylene glycol, diethylene glycol, triethylene glycol, ethanolamine, diethanolamine, triethanolamine, hindered cyclic amines, acetonitrile, n-methylpyrrolidone, dimethyl formamide, and combinations thereof.

To obtain a substantial degree of effectiveness, the water absorbent should contain little non-water absorbing components. For example, the water absorbent should contain at least about 75 weight percent water absorbing components. Desirably, the water absorbent contains at least about 90 weight percent, preferably at least about 95 weight percent, and most preferably at least about 98 weight percent water absorbent.

When a water absorbent is used to reduce the concentration of water in the initial effluent stream prior to separation of the DME, a wash type of process using a wash vessel can be used. In essence, a wash process is one in which the initial effluent stream is contacted with water absorbent such that a substantial amount of the water is removed, i.e., washed out, from the initial effluent stream. The amount of absorbent added to the wash vessel should be sufficient to substantially reduce free water formation (i.e., formation of a separate liquid phase), particularly in the vessel in which the separation of the DME from the olefin components takes place. In this embodiment, it is desirable that water absorbent be added to the wash vessel at a mole ratio of absorbent compound to total olefin feed to the wash vessel of about 1:2 to about 1:200. Preferably, the absorbent is added at a mole ratio of from about 1:5 to about 1:100, and more preferably from about 1:10 to about 1:50.

Although the olefin stream can come from any conventional source which contains DME, the invention is particularly suited to removing DME from initial effluent stream made from an oxygenate to olefin process or, particularly, from an MTO process. In one embodiment of this invention, an initial effluent stream containing DME is obtained by contacting oxygenate feedstock with a molecular sieve catalyst, as described below.

The First Separation Unit

According to the present invention, a first stream, e.g., the initial effluent stream, comprising DME, ethane, ethylene and propylene is directed to a first separation unit. The first separation unit preferably includes one or more distillation and/or fractionation columns, absorbers and/or extractive distillation columns that are designed to form one or more overhead streams comprising the ethane, ethylene, propylene, and optionally propane and/or acetylene, and one or more bottoms streams comprising at least a portion of the DME. The first separation unit preferably subjects the first stream to conditions, e.g., temperature and pressure, that are effective to separate the first stream into a first fraction and a second fraction. The term "fraction," as used herein, is not limited to a stream that is formed by a fractionation or distillation process, and any of a number of known separation processes may be used to form the fractions according to the present invention. Furthermore, it is to be understood that a side draw stream optionally may be implemented in a separation unit when reference is made herein to an overhead or bottoms stream.

The first fraction, which preferably is an overhead fraction, contains a majority of the ethane, ethylene and propylene, individually or collectively, that was present in the first stream. More preferably, the first fraction comprises at least about 60 weight percent, more preferably at least about 75 weight percent, and most preferably at least about 90 weight percent of the ethane, ethylene and propylene, individually or collectively, that was present in the first stream.

If the first stream includes propane, then the first fraction optionally contains a majority of the propane that was present in the first stream. More specifically, in one embodiment, the first fraction comprises at least about 60 weight percent, more preferably at least about 75 weight percent, and most preferably at least about 90 weight percent of the propane that was present in the first stream. If the first stream includes acetylene, then the first fraction preferably contains a majority of the acetylene that was present in the first stream. More preferably, the first fraction comprises at least about 60 weight percent, more preferably at least about 75 weight percent, and most preferably at least about 90 weight percent of the acetylene that was present in the first stream.

In one embodiment, the invention includes removing oxygenated components such as methanol and DME from the initial effluent stream in the first separation unit. This embodiment is particularly beneficial for removing DME from an ethylene and/or propylene containing stream so that the ethylene and/or propylene can be polymerized without poisoning catalyst used in the polymerization reaction. Preferably, this separation step occurs in the first separation unit. Additionally or alternatively, however, further removal of these or other light oxygenates may occur in additional downstream separation steps. The recovered light oxygenates optionally are recycled as feedstock to the MTO reactor.

In one embodiment, the second fraction, which preferably is a bottoms stream, contains a majority of the DME that was present in the first stream. Optionally, at least about 75 weight percent of the DME in the provided initial effluent stream will be separated out in the second fraction. Preferably, at least about 85 weight percent of the DME in the provided olefin stream will be separated out in the second fraction, more preferably at least about 95 weight percent, and most preferably at least about 99 weight percent.

The second fraction may also contain some propane from the first stream. Depending on the design of the first separation unit, the second fraction optionally contains less than about 50 weight percent, more preferably less than about 35 weight percent, and most preferably less than about 25 weight percent of the propane that was present in the first stream. In terms of lower range limitations, the second fraction may include at least about 5 weight percent, more preferably at least about 10 weight percent, more preferably at least about 20, and most preferably at least about 30 weight percent of the propane that was present in the initial effluent stream. In another embodiment, the second fraction contains at least a majority of the propane that was present in the initial effluent. In this embodiment, the second fraction optionally contains at least about 60 weight percent, at least about 75 weight percent, or at least about 80 weight percent of the propane present in the initial effluent stream.

According to the present invention, oxygenated contaminants, particularly including DME, are removed from the provided initial effluent stream at low or high pressure. An advantage of using a low pressure separation is that lower temperatures can be obtained in the heavier fractions separated during the separation process. A benefit of lower temperatures is that there will be fewer equipment fouling problems. In addition, such a process will use a lower energy input to run associated operating equipment such as reboilers and condensers. Another advantage in low pressure separation is that less energy will be required to maintain system separation pressure. This means that compressors having fewer stages can be more readily utilized.

An advantage of using a high pressure separation is that separation of olefins can be accomplished at higher temperatures. By taking advantage of higher temperature separation, less refrigeration is required to recover lighter olefins such as ethylene and propylene. The practical result is a substantial savings in energy. Another advantage of high pressure separation is that clathrate and free water formation can be more easily controlled in the separation equipment. This is particularly advantageous when distillation columns having internal trays are used as the separation equipment, since internal trays are prone to collect water and clathrates. If an excessive amount of water and/or clathrates are collected, the trays can break apart or collapse, causing severe equipment damage.

In general, the process of separating DME from an initial effluent stream at low pressure comprises providing an initial effluent stream which contains ethylene, ethane, propylene, and DME, and separating at least a majority, i.e., greater than 50 weight percent, of the DME present in the olefin stream. The initial effluent stream can come from any conventional source. However, this process is particularly effective in separating DME from effluent streams formed from an oxygenate to olefin process, and particularly from an MTO reaction process.

The initial effluent stream preferably is separated into a first fraction and a second fraction, with a majority of ethylene and/or propylene being separated in the first fraction and a majority of the DME being separated in the second fraction. In one embodiment, the separation is carried out at a pressure of less than 200 psig (1,480 kPa absolute). Preferably, separation is carried out at a pressure of from about 100 psig (791 kPa absolute) to about 200 psig (1,480 kPa absolute), more preferably from about 120 psig (929 kPa absolute) to about 180 psig (1,342 kPa absolute).

As indicated above, the separation can also be performed at a high pressure. For example, in the high pressure separation embodiment, the initial effluent stream can be separated into a first fraction and a second fraction at a pressure of at least about 200 psig (1,480 kPa absolute). Preferably, the high pressure separation is carried out at a pressure of from about 200 psig (1,480 kPa absolute) to about 290 psig (2,100 kPa absolute), more preferably from about 250 psig (1,825 kPa absolute) to about 290 psig (2,100 kPa absolute).

In the high pressure separation embodiment, the actual upper pressure limit of the separation process will typically depend upon the temperature at which the second fraction is separated. The second fraction optionally contains DME and other hydrocarbons having boiling points higher than DME, for example $C_4+$ components. It is desirable to keep the compounds in the second fraction sufficiently low in temperature so as not to cause chemical degradation or fouling problems in other downstream separation and treating equipment.

In another embodiment of the invention, the separation process is performed in a distillation column such that the first or overhead stream is at a temperature of not greater than about 30° F. (−1.1° C.). Preferably the first or overhead stream is at a temperature of about 0° F. (−17.8° C.) to about 30° F. (−1.1° C.), more preferably about 10° F. (−12.2° C.) to about 25° F. (−3.9° C.). In this embodiment, separation will be such that the second fraction will have an average temperature of not greater than about 250° F. (121° C.), preferably not greater than about 240° F. (116° C.), and more preferably not greater than about 230° F. (110° C.).

It is desirable in this invention that the second or bottoms fraction of the distillation column be maintained at a temperature level to reduce fouling problems. In one embodiment, the second fraction is at an average temperature of not greater than about 210° F. (99° C.), preferably not greater than about 200° F. (93° C.), and more preferably not greater than about 190° F. (88° C.).

It is further desirable in this invention that water absorbent, as described above, be added to the first separation unit in which the separation of the oxygenated contaminants from the provided initial effluent stream is performed. The addition of water absorbent directly to the separation vessel can be of additional benefit in reducing free water and/or clathrate formation in the vessel.

In one embodiment of the invention, water absorbent is added to the oxygenate separation vessel, e.g., the first separation unit, in an amount sufficient to substantially reduce oxygenate content (e.g., DME) or clathrate formation. It is preferred that water absorbent be added to the vessel at a molar ratio of water absorbent to total olefin feed entering the separation vessel of about 4:1 to about 1:5,000. Higher molar ratios of water absorbent to total olefin feed are desirable for reducing oxygenate content; preferably from about 4:1 to about 1:1, more preferably from about 3:1 to about 1.2:1, and most preferably from about 2.5:1 to about 1.5:1. Lower molar ratios of water absorbent to total olefin feed are desirable for reducing clathrate formation; preferably from about 1:1 to about 1:5,000, more preferably from about 1:100 to about 1:4,000, and most preferably from about 1:500 to about 1:3,000.

In one embodiment of this invention, separation is by conventional distillation. Distillation is carried out using a vessel or tower having internal packing or trays that creates a temperature difference from top to bottom of the tower. The upper portion of the tower is the cooler portion, and higher volatile components in the feed exit from the top of the tower.

In this invention it is desirable to obtain high concentrations of ethylene and propylene from an initial effluent stream containing DME. In one embodiment, the DME is separated from the ethylene and propylene in the initial effluent stream. In this embodiment, the ethylene and propylene are recovered in a first fraction, and the DME is recovered in a second fraction. Typically, the first fraction will be the overhead or side fraction of a distillation column, and the second fraction will be a bottoms fraction or additional side fraction of a distillation column.

In one embodiment of the invention, a majority of the ethylene and propylene in the provided initial effluent stream will be separated in a first fraction and a majority of the DME and other oxygenates in the provided olefin stream will be separated in a second fraction. Preferably, the first fraction will contain at least about 75 weight percent of the ethylene and propylene in the provided olefin stream, more preferably at least about 85 weight percent, and most preferably at least about 95 weight percent.

A majority of the propane in the provided initial effluent stream, if any, can be separated out in either the first or second fraction. If the majority of the propane is contained in the first fraction, then there will be less separation of heavier products needed in the second fraction. However, there can be slightly increased levels of DME in the first fraction when a majority of the propane is in the first fraction. In this embodiment, at least about 60 weight percent of the propane in the provided initial effluent stream, preferably at least about 70 weight percent, and more preferably at least about 80 weight percent will be in the first fraction, and the first fraction will contain not greater than about 50 wppm, preferably not greater than about 25 wppm, more preferably not greater than about 10 wppm DME, and most preferably not greater than about 5 wppm DME.

If a majority of the propane in the provided initial effluent stream is separated out in the second fraction, then the concentration of DME in the first fraction will be significantly lower. In this embodiment, at least about 60 weight percent of the propane in the provided olefin stream, preferably at least about 70 weight percent, and more preferably at least about 80 weight percent will be in the second fraction, and the second fraction will contain not greater than about 25 wppm, preferably not greater than about 15 wppm, more preferably not greater than about 5 wppm ether, and most preferably not greater than about 1 wppm DME.

In another embodiment of the invention, the second fraction will also contain some hydrocarbon compounds having four or more carbons. These compounds are also known as $C_4+$ components. The amount of $C_4+$ components in the second fraction can vary, particularly depending upon the amount of propane in the second fraction. For example, the second fraction optionally contains from about 5 weight percent to about 90 weight percent $C_4+$ components. Preferably, the second fraction contains from about 25 weight percent to about 80 weight percent $C_4+$ components, more preferably from about 35 weight percent to about 75 weight percent $C_4+$ components.

It is of further advantage in this invention to operate the separation vessel, e.g., the first separation unit, at a temperature and pressure to separate out of the provided initial effluent stream at least a majority (i.e., at least 50 weight percent) of any propadiene which might be present. In this embodiment, the propadiene would preferably be separated out in the second fraction along with DME. Preferably, at least about 75 weight percent, more preferably at least about 85 weight percent, and most preferably at least about 95 weight percent of the propadiene would be separated out. Separating out any propadiene in this manner would necessarily include separating out a substantial portion of any methyl acetylene which can also be present in the provided initial effluent stream. This is because methyl acetylene has a lower normal boiling point than propadiene and DME. Removing propadiene and methyl acetylene from the provided initial effluent stream would provide a substantial benefit in that the first fraction containing the ethylene and/or propylene would have a very high concentration of mono-olefinic compounds. Such a stream would need little if any hydro processing, which might typically be needed to reduce the number of multiply unsaturated or alkylene compounds recovered in the first fraction.

This separation technique is particularly advantageous for treating the ethylene and propylene streams contained in the first fraction to remove entrained acid gases such as $CO_2$ which can also be present in such fraction. The advantage is that in this invention the separated ethylene and propylene streams will contain relatively few hydrocarbon components that cause fouling problems in such acid gas treatment systems.

Solid or liquid acid gas treatment systems can be used in this invention. In either system, the acid gas is removed from the ethylene and/or propylene stream in the first fraction by contacting the first fraction with an acid gas absorbent or adsorbent. Examples of such absorbents or adsorbents include amines, potassium carbonate, caustic, alumina, molecular sieves, and membranes, particularly membranes formed of polysulfone, polyimid, polyamide, glassy polymer and cellulose acetate. Solutions containing amines and caustic compounds are preferred, with caustic compounds being more preferred.

Aqueous amine solutions which are useful in this invention can contain any amine compound or compounds suitable for acid gas absorption. Examples include alkanolamines, such as triethanolamine (TEA); methyldiethanolamine (MDEA); diethanolamine (DEA); monoethanolamine (MEA); diisopropanolamine (DIPA); and hydroxyaminoethyl ether (DGA). Effective concentrations can range from about 0.5 to about 8 moles of amine per liter of aqueous solution.

Piperazine and/or monomethylethanolamine (MMEA) can be added to aqueous amine solutions to enhance their absorption capabilities. These additives can be included in the aqueous solution at a concentration of from about 0.04 to about 2 moles per liter of aqueous solution.

Caustic compounds which can be used in this invention are alkaline compounds which are effective in removing acid gas from an initial effluent stream. Examples of such alkaline compounds include sodium hydroxide and potassium hydroxide.

Following acid gas treating, it is desirable to remove additionally entrained material in the treated ethylene and/or propylene using a water wash. Conventional equipment can be used. It is desirable, however, to further remove additional water from the separated ethylene and/or propylene streams.

In one embodiment of this separation technique, the ethylene and propylene in the first fraction is water washed, i.e., contacted with a water stream, prior to acid gas treating. This contacting is particularly advantageous when water absorbent is added to the oxygenate separation vessel, e.g., the first separation unit, as water absorbent can carry over into the first or overhead fraction. Water washing would then be conducted to remove a substantial portion of water absorbent carry over prior to acid gas treating.

This invention further includes an optional drying embodiment. In this embodiment, a solid or liquid drying system can be used to remove water and/or additional oxygenated hydrocarbon from the first fraction.

In the solid drying system, the ethylene and/or propylene having been separated in a first fraction, and optionally acid gas treated and water washed, is contacted with a solid adsorbent to further remove water and oxygenated hydrocarbon to very low levels. Typically, the adsorption process is carried out in one or more fixed beds containing a suitable solid adsorbent.

Adsorption is useful for removing water and oxygenated hydrocarbons to very low concentrations, and for removing oxygenated hydrocarbons that are not normally removed by using other treatment systems. Preferably, an adsorbent system used as part of this invention has multiple adsorbent beds. Multiple beds allow for continuous separation without the need for shutting down the process to regenerate the solid adsorbent. For example, in a three bed system typically one bed is on-line, one bed is regenerated off-line, and a third bed is on stand-by.

The specific adsorbent solid or solids used in the adsorbent beds depends on the types of contaminants being removed. Examples of solid adsorbents for removing water and various polar organic compounds, such as oxygenated hydrocarbons and absorbent liquids, include aluminas, silica, 3 Å molecular sieves, 4 Å molecular sieves, and alumino-silicates. Beds containing mixtures of these sieves or multiple beds having different adsorbent solids can be used to remove water, as well as a variety of oxygenated hydrocarbons.

In this separation technique, one or more adsorption beds can be arranged in series or parallel. In one example of a series arrangement, a first bed is used to remove the smallest and most polar molecules which are the easiest to remove. Subsequent beds for removing larger less polar oxygenated species are next in series. As a specific example of one type of arrangement, water is first selectively removed using a 3 Å molecular sieve. This bed is then followed by one or more beds containing one or more less selective adsorbents such as a larger pore molecular sieve e.g. 13× and/or a high surface area active alumina such as Selexorb CD (Alcoa tradename).

In another embodiment, the first bed is a 3.6 Å molecular sieve capable of selectively removing both water and methanol. This bed can then be followed by one or more 13× or active alumina beds as described above.

The adsorbent beds can be operated at ambient temperature or at elevated temperature as required, and with either upward or downward flow. Regeneration of the adsorbent materials can be carried out by conventional methods including treatment with a stream of a dry inert gas such as nitrogen at elevated temperature.

In the liquid drying system, a water absorbent is used to remove water from the first fraction. The water absorbent can be any liquid effective in removing water from an olefin stream. Preferably, the water absorbent is the same as that previously described.

Preferably the olefin from the adsorption beds contains less than about 100 wppm water, more preferably less than about 10 wppm, and most preferably less than 1 wppm. Preferably less than about 10 wppm DME is present in the stream leaving the adsorption beds, more preferably less than about 5 wppm, and most preferably less than about 1 wppm.

U.S. patent applications Ser. Nos. 10/125,138, filed Apr. 18, 2002, and 10/124,859, filed on Apr. 18, 2002, the entireties of which are incorporated herein by reference, disclose particularly desirable first separation units that may be implemented in the separation processes of the present invention.

C2/C3 Separation Followed by Light Ends Removal

In a first embodiment of the present invention, C2/C3 separation is followed by light ends removal. In this embodiment, the first fraction from the first separation unit, described above, is directed to a second separation unit, e.g., a C2/C3 splitter, for further processing. The second separation unit preferably subjects the first fraction to conditions, e.g., temperature and pressure, that are effective to separate the first fraction into a third fraction and a fourth fraction. The third fraction, which preferably is an overhead fraction, contains a majority of the ethane and ethylene, individually or collectively, that was present in the first fraction. More preferably, the third fraction comprises at least about 60 weight percent, more preferably at least about 75 weight percent, and most preferably at least about 90 weight percent of the ethane and ethylene, individually or collectively, that was present in the first fraction. If the first fraction includes acetylene, then the third fraction preferably contains a majority of the acetylene that was present in the first fraction. More preferably, the third fraction comprises at least about 60 weight percent, more preferably at least about 75 weight percent, and most preferably at least about 90 weight percent of the acetylene that was present in the first fraction. The fourth fraction, which preferably is a bottoms fraction, contains a majority of the propylene that was present in the first fraction. More preferably, the fourth fraction comprises at least about 60 weight percent, more preferably at least about 75 weight percent, and most preferably at least about 90 weight percent of the propylene that was present in the first fraction. If the first fraction includes propane, then the fourth fraction preferably contains a majority of the propane that was present in the first fraction. More preferably, the fourth fraction comprises at least about 60 weight percent, more preferably at least about 75 weight percent, and most preferably at least about 90 weight percent of the propane that was present in the first fraction. The second separation unit preferably includes one or more distillation and/or fractionation columns, absorbers and/or extractive distillation columns that are designed to form one or more overhead streams comprising ethane and ethylene, and optionally acetylene, and one or more bottoms streams comprising propylene, and optionally propane.

If the first stream, the first fraction and the third fraction contain light ends such as methane, carbon monoxide and hydrogen, the third fraction preferably is directed to a third separation unit, e.g., a light ends removal unit, for further processing. The third separation unit preferably subjects the third fraction to conditions, e.g., temperature and pressure, that are effective to separate the third fraction into a fifth fraction and a sixth fraction. The fifth fraction, which preferably is an overhead fraction, contains a majority of the light ends, individually or collectively, that was present in the third fraction. More preferably, the fifth fraction comprises at least about 60 weight percent, more preferably at least about 75 weight percent, and most preferably at least about 90 weight percent of the light ends, individually or collectively, was present in the third fraction. The sixth fraction, which preferably is a bottoms fraction, contains a majority of the ethane and ethylene, individually or collectively, that was present in the third fraction. More preferably, the sixth fraction comprises at least about 60 weight percent, more preferably at least about 75 weight percent, and most preferably at least about 90 weight percent of the ethane and ethylene, individually or collectively, that was present in the third fraction. The third separation unit preferably includes one or more distillation and/or fractionation columns, absorbers and/or extractive distillation columns that are designed to form one or more overhead streams comprising methane and any other light ends, and one or more bottoms streams comprising ethane and ethylene.

Preferably, the sixth fraction is directed to a fourth separation unit, e.g., a C2 splitter, for further processing. The fourth separation unit preferably subjects the sixth fraction to conditions, e.g., temperature and pressure, that are effective to separate the sixth fraction into a seventh fraction and an eighth fraction. The seventh fraction, which preferably is an overhead fraction, contains a majority of the ethylene that was present in the sixth fraction. More preferably, the seventh fraction comprises at least about 60 weight percent, more preferably at least about 75 weight percent, and most preferably at least about 90 weight percent of the ethylene that was present in the sixth fraction. The eighth fraction, which preferably is a bottoms fraction, contains a majority of the ethane that was present in the sixth fraction. More preferably, the eighth fraction comprises at least about 60 weight percent, more preferably at least about 75 weight percent, and most preferably at least about 90 weight percent of the ethane that was present in the sixth fraction. The fourth separation unit preferably includes one or more distillation and/or fractionation columns, absorbers and/or extractive distillation columns that are designed to form one or more overhead streams comprising polymerization grade ethylene, and one or more bottoms streams comprising ethane.

The fourth fraction contains propylene suitable for polymerization, but also contains a minor amount of propane. Optionally, the fourth fraction from the second separation unit is directed to a fifth separation unit, e.g., a C3 splitter, for additional propane removal. The fifth separation unit preferably subjects the fourth fraction to conditions, e.g., temperature and pressure, that are effective to separate the fourth fraction into a ninth fraction and a tenth fraction. The ninth fraction, which preferably is an overhead fraction, contains a majority of the propylene that was present in the fourth fraction. More preferably, the ninth fraction comprises at least about 60 weight percent, more preferably at least about 75 weight percent, and most preferably at least about 90 weight percent of the propylene that was present in the fourth fraction. The tenth fraction, which preferably is a bottoms fraction, contains a majority of the propane, if any, that was present in the fourth fraction. More preferably, the tenth fraction comprises at least about 60 weight percent, more preferably at least about 75 weight percent, and most preferably at least about 90 weight percent of the propane, if any, that was present in the fourth fraction. The fifth separation unit preferably includes one or more distillation and/or fractionation columns, absorbers and/or extractive distillation columns that are designed to form one or more overhead streams comprising polymerization grade propylene, and one or more bottoms streams comprising propane, if any was present in the fourth fraction.

In another embodiment, the fifth separation unit functions as a propane purge tower rather than a C3 splitter. In this embodiment, the propane purge tower operates in a similar manner as the C3 splitter, discussed above, although the propane purge tower includes fewer trays than a C3 splitter thereby providing a commensurate decrease in height and start-up costs. As a propane purge tower, the fifth separation unit preferably is a distillation column adapted to separate some of the propane from the fourth fraction. Specifically, the fifth separation unit separates the fourth fraction into a ninth fraction, which contains a majority of the propylene and some of the propane that was present in the fourth fraction, and a tenth fraction, which preferably contains some of the propane and optionally any residual C4+ components that were present in the fourth fraction. Ideally, the ninth fraction contains at least about 60 weight percent, more preferably at least about 75 weight percent, and most preferably at least about 90 weight percent of the propylene that was present in the fourth fraction. The ninth fraction also preferably contains less than about 90 weight percent, more preferably less than about 50 weight percent, and most preferably less than about 10 weight percent of the propane that was present in the fourth fraction. The tenth fraction preferably contains at least about 0.1 weight percent, more preferably at least about 0.5 weight percent, and most preferably at least about 5.0 weight percent of the propane that was present in the fourth fraction. Because propane is unreactive in most polymerization units, the ninth fraction is suitable for polymerization. The tenth fraction optionally is burned as fuel. In an alternative embodiment, at least a portion of the tenth fraction is recycled to the first separation unit.

DME is particularly difficult to remove from the initial effluent stream. One preferred embodiment of the invention includes removing DME from the initial effluent stream in a plurality of steps (preferably in two steps). In this embodiment, the first separation unit, described above, removes a first portion of DME from the initial effluent stream in the second fraction. A second portion of the DME from the initial effluent stream remains in the first fraction. Thus, both the first and second fractions contain a detectable amount of DME. In terms of lower range limitations, the first fraction may include at least about 5 weight percent, more preferably at least about 10 weight percent, more preferably at least about 20 weight percent, and most preferably at least about 60 weight percent of the DME that was present in the initial effluent stream. The second fraction may include at least about 5 weight percent, more preferably at least about 10 weight percent, more preferably at least about 20 weight percent, and most preferably at least about 30 weight percent of the DME that was present in the initial effluent stream. The DME remaining in the first fraction then passes through the second separation unit and into the fifth separation unit via the fourth fraction. The fifth separation unit then separates the fourth fraction into a ninth fraction containing a majority of the propylene that was present in the fourth fraction, and a tenth fraction containing a majority of the propane and DME that was present in the fourth fraction. Thus, the first separation unit and the fifth separation unit act to remove DME. In one embodiment, the second fraction contains from about 10 weight percent to about 40 weight percent, more preferably from about 15 to about 35 weight percent, and most preferably from about 20 to about 30 weight percent of the DME that was present in the initial effluent stream. The tenth fraction from the fifth separation unit preferably contains from about 60 weight percent to about 90 weight percent, more preferably from about 65 to about 85 weight percent, and most preferably from about 70 to about 80 weight percent of the DME that was present in the initial effluent stream.

Acetylene and other multiply unsaturated species are generally undesirable compounds, which preferably are converted to a more desirable form in one or more hydrogenation converters, e.g., acetylene converters. The hydrogenation converters are adapted to at least partially saturate acetylene or other multiply unsaturated species to, for example, alkenes and/or alkanes. Specifically, in a hydrogenation converter, multiply unsaturated species such as acetylene contact hydrogen and/or carbon monoxide under conditions effective to at least partially hydrogenate the multiply unsaturated species. The one or more acetylene converters may be adapted to at least partially hydrogenate other components as well. A non-limiting list of other exemplary components that may be at least partially hydrogenated in a hydrogenation converter includes: methyl acetylene and propadiene. Preferably, the hydrogenation converter converts acetylene to ethylene; methyl acetylene to propylene; and propadiene to propylene. Desirable components such as ethylene and propylene preferably pass through the one or more hydrogenation converters unaltered. According to the present invention, the one or more hydrogenation converters may be oriented in a variety of locations, although the converters ideally are oriented along one or more streams that contain acetylene. In the separation sequence described above, the one or more hydrogenation converters preferably receives and processes multiply unsaturated species from the fourth fraction, the fifth fraction and/or the seventh fraction, as these fractions contain the highest concentrations of acetylene.

FIG. 1 illustrates this embodiment of the present invention. As shown, initial effluent stream 101, which contains ethane, ethylene, DME, propane, and propylene is directed to first separation unit 102, which preferably is a distillation column adapted to separate ethylene and propylene, as well as lighter components, from the DME and heavier components, including any $C_4+$ components, and methanol. This means that both ethylene and propylene are recoverable in a first fraction 104, with the DME and $C_4+$ components being recoverable in a second fraction 105. Propane that is present in the initial effluent stream 101 is recoverable in either the first or second fraction, or both, depending upon how low a concentration of DME in the first fraction is desired. Additional methanol optionally is added to the first separation unit 102 though line 103 to reduce hydrate and/or free water formation in the first separation unit 102. The first separation unit 102 optionally includes a reflux line and/or a reboiler line and corresponding heat exchangers, not shown, to facilitate separation of these components. Specifically, the first separation unit 102 separates the initial effluent stream 101 into a first fraction 104, which contains a majority of the ethane, ethylene, propane and propylene that was present in the initial effluent stream 101, and a second fraction 105, which preferably contains a majority of the DME that was present in the initial effluent stream 101. The second fraction 105 also preferably contains a majority of the C4+ components and methanol, if any, that was present in the initial effluent stream 101.

Optionally, first fraction 104 is directed to a caustic wash unit to remove carbon dioxide, a water wash column, and/or a drying unit, not shown. Reverting to FIG. 1, first fraction 104 preferably is directed to a second separation unit 106. The second separation unit 106 preferably is a distillation column adapted to separate C2− components from C3+ components. Specifically, the second separation unit 106 separates the first fraction 104 into a third fraction 107, which contains a majority of the ethane and ethylene that was present in the first fraction 104, and a fourth fraction 108, which preferably contains a majority of the propane and propylene that was present in the first fraction 104. The second separation unit 106 optionally includes a reflux line and/or a reboiler line and corresponding heat exchangers, not shown, to facilitate separation of the C2− components from the C3+ components.

Third fraction 107 preferably is introduced into demethanizer feed train 112. Demethanizer feed train 112 is a "cold box" that preferably is formed of a series of coolers, e.g., Core Exchangers, and knock out drums, not shown, that cool third fraction 107 and form a plurality of cooled streams 114A–C. Cooled streams 114A–C may be in liquid and/or vapor form. Preferably, cooled streams 114A–C are directed to a third separation unit 115 for further processing. The third separation unit 115 preferably is a distillation column adapted to separate light ends such as methane, hydrogen and/or carbon monoxide from ethane and ethylene. Specifically, the third separation unit 115 separates the cooled streams 114A–C, collectively, into a fifth fraction 116, which contains a majority of the light ends that were present in the cooled streams 114A–C, and a sixth fraction 117, which preferably contains a majority of the ethane and ethylene that was present in the cooled streams 114A–C. The third separation unit 115 optionally includes a reflux line and/or a reboiler line and corresponding heat exchangers, not shown, to facilitate separation of the light ends from ethane and ethylene. In one embodiment, the fifth fraction 116 is directed to the demethanizer feed train 112 for use as a cooling medium.

The sixth fraction 117 is directed to a fourth separation unit 124 for further processing. The fourth separation unit preferably is a distillation column adapted to separate ethylene from ethane. Specifically, the fourth separation unit 124 separates the sixth fraction 117 into a seventh fraction 125, which contains a majority of the ethylene that was present in the sixth fraction 117, and an eighth fraction 126, which preferably contains a majority of the ethane that was present in the sixth fraction 117. The fourth separation unit 124 optionally includes a reflux line and/or a reboiler line and corresponding heat exchangers, not shown, to facilitate separation of ethylene from ethane. Seventh fraction 125 contains relatively pure ethylene, which may be directed to a polymerization unit for polymerization. The eighth fraction 126 preferably is directed to the demethanizer feed train 112 for use as a cooling medium. Optionally, the eighth fraction 126 is combined with the cooling medium from fifth fraction 116, as shown by the broken line in demethanizer feed train 112. After cooling the vapor from third fraction 107 in the demethanizer feed train 112, the cooling mediums exit the demethanizer feed train 112 through tail gas line 113.

The fourth fraction 108 contains mostly propylene and a minor amount of propane, and is well-suited for polymerization disposition. If very high quality propylene is desired, then the fourth fraction 108 optionally is introduced into fifth separation unit 136. The fifth separation unit 136 preferably is a distillation column adapted to separate propylene from propane. The fifth separation unit 136 thus may operate as a C3 splitter. Specifically, the fifth separation unit 136 separates the fourth fraction 108 into a ninth fraction 137, which contains a majority of the propylene that was present in the fourth fraction 108, and a tenth fraction 138, which preferably contains a majority of the propane and optionally any residual C4+ components that were present in the fourth fraction 108. The fifth separation unit 136 optionally includes a reflux line and/or a reboiler line and corresponding heat exchangers, not shown, to facilitate separation of the propylene from the propane. The ninth fraction 137 contains very high quality propylene, which is suitable for polymerization. The tenth fraction 138 preferably is burned as fuel.

In another embodiment, the fifth separation unit 136 functions as a propane purge tower rather than a C3 splitter. The propane purge tower operates in a similar manner as the C3 splitter, discussed above, although the propane purge tower includes fewer trays than a C3 splitter thereby providing a commensurate decrease in height and start-up costs. In this embodiment, the fifth separation unit 136 preferably is a distillation column adapted to separate some of the propane from the fourth fraction 108. Specifically, the fifth separation unit 136 separates the fourth fraction 108 into a ninth fraction 137, which contains a majority of the propylene and some of the propane that was present in the fourth fraction 108, and a tenth fraction 138, which preferably contains some of the propane and optionally any residual C4+ components that were present in the fourth fraction 108. The fifth separation unit 136 in this embodiment also optionally includes a reflux line and/or a reboiler line and corresponding heat exchangers, not shown, to facilitate partial separation of propane from propylene. The ninth fraction 137 contains high quality propylene, which is suitable for polymerization. The tenth fraction 138 preferably is burned as fuel.

If the initial effluent stream 101 contains acetylene, methyl acetylene, propadiene, or other multiply unsaturated components, then the system of the present invention preferably includes a hydrogenation converter, e.g., an acetylene converter, not shown. If incorporated into the present invention, the hydrogenation converter preferably receives and processes one or more of the following streams: the first fraction 104, the third fraction 107, and/or the sixth fraction 117. In the hydrogenation converter, acetylene contacts hydrogen and carbon dioxide under conditions effective to convert at least a portion of the acetylene to ethylene. Similarly, methyl acetylene and/or propadiene contact hydrogen and carbon dioxide under conditions effective to convert at least a portion of the methyl acetylene and/or propadiene to propylene. Components other than acetylene, methyl acetylene and propadiene that are present in the above-identified streams preferably pass unaltered through the hydrogenation converter(s). The resulting acetylene-depleted streams are then processed as described above with reference to FIG. 1.

Light Ends Removal Followed by C2/C3 Separation

In another embodiment of the present invention, light ends removal is followed by C2/C3 separation. In this embodiment, if the first fraction from the first separation unit, described above, includes methane and/or any other light ends, then the first fraction from the first separation unit preferably is directed to a second separation unit, which operates as a light ends removal unit. The second separation unit preferably subjects the first fraction to conditions, e.g., temperature and pressure, that are effective to separate the first fraction into a third fraction and a fourth fraction. The third fraction, which preferably is an overhead fraction, contains a majority of the light ends, individually or collectively, that were present in the first fraction. More preferably, the third fraction comprises at least about 60 weight percent, more preferably at least about 75 weight percent, and most preferably at least about 90 weight percent of the light ends, individually or collectively, that were present in the first fraction. The fourth fraction, which preferably is a bottoms fraction, contains a majority of the ethane, ethylene and propylene, individually or collectively, that was present in the first fraction. More preferably, the fourth fraction comprises at least about 60 weight percent, more preferably at least about 75 weight percent, and most preferably at least about 90 weight percent of the ethane, ethylene and propylene, individually or collectively, that was present in the first fraction. If the first fraction contained propane and/or acetylene, the fourth fraction also preferably contains at least about 60 weight percent, more preferably at least about 75 weight percent, and most preferably at least about 90 weight percent of the propane and/or acetylene, individually or collectively, that was present in the first fraction. The second separation unit preferably includes one or more distillation and/or fractionation columns, absorbers and/or extractive distillation columns that are designed to form one or more overhead streams comprising the methane and other light ends, and one or more bottoms streams comprising the ethane, ethylene and propylene, and optionally propane and/or acetylene.

In this embodiment, the fourth fraction is directed to a third separation unit, e.g., a C2/C3 splitter. The third separation unit preferably subjects the fourth fraction to conditions, e.g., temperature and pressure, that are effective to separate the fourth fraction into a fifth fraction and a sixth fraction. The fifth fraction, which preferably is an overhead fraction, contains a majority of the ethane and ethylene, individually or collectively, that was present in the fourth fraction. More preferably, the fifth fraction comprises at least about 60 weight percent, more preferably at least about 75 weight percent, and most preferably at least about 90 weight percent of the ethane and ethylene, individually or collectively, that was present in the fourth fraction. If the fourth fraction includes acetylene, then the fifth fraction preferably contains a majority of the acetylene that was present in the fourth fraction. More preferably, the fifth fraction comprises at least about 60 weight percent, more preferably at least about 75 weight percent, and most preferably at least about 90 weight percent of the acetylene that was present in the fourth fraction. The sixth fraction, which preferably is a bottoms fraction, contains a majority of the propylene that was present in the fourth fraction. More preferably, the sixth fraction comprises at least about 60 weight percent, more preferably at least about 75 weight percent, and most preferably at least about 90 weight percent of the propylene that was present in the fourth fraction. If the fourth fraction includes propane, then the sixth fraction preferably contains a majority of the propane that was present in the fourth fraction. More preferably, the sixth fraction comprises at least about 60 weight percent, more preferably at least about 75 weight percent, and most preferably at least about 90 weight percent of the propane that was present in the fourth fraction. The third separation unit preferably includes one or more distillation and/or fractionation columns, absorbers and/or extractive distillation columns that are designed to form one or more overhead streams comprising the ethane and ethylene, and optionally acetylene, and one or more bottoms streams comprising the propylene, and optionally propane.

Preferably, the fifth fraction is directed to a fourth separation unit, e.g., a C2 splitter, for further processing. The fourth separation unit preferably subjects the fifth fraction to conditions, e.g., temperature and pressure, that are effective to separate the fifth fraction into a seventh fraction and an eighth fraction. The seventh fraction, which preferably is an overhead fraction, contains a majority of the ethylene that was present in the fifth fraction. More preferably, the seventh fraction comprises at least about 60 weight percent, more preferably at least about 75 weight percent, and most preferably at least about 90 weight percent of the ethylene that was present in the fifth fraction. The eighth fraction, which preferably is a bottoms fraction, contains a majority of the ethane that was present in the fifth fraction. More preferably, the eighth fraction comprises at least about 60 weight percent, more preferably at least about 75 weight percent, and most preferably at least about 90 weight percent of the ethane that was present in the fifth fraction. The fourth separation unit preferably includes one or more distillation and/or fractionation columns, absorbers and/or extractive distillation columns that are designed to form one or more overhead streams comprising polymerization grade ethylene, and one or more bottoms streams comprising ethane.

The sixth fraction contains propylene suitable for polymerization, but also contains a minor amount of propane.

Optionally, the sixth fraction from the third separation unit is directed to a fifth separation unit, e.g., a C3 splitter, for additional propane removal. The fifth separation unit preferably subjects the sixth fraction to conditions, e.g., temperature and pressure, that are effective to separate the sixth fraction into a ninth fraction and a tenth fraction. The ninth fraction, which preferably is an overhead fraction, contains a majority of the propylene that was present in the sixth fraction. More preferably, the ninth fraction comprises at least about 60 weight percent, more preferably at least about 75 weight percent, and most preferably at least about 90 weight percent of the propylene that was present in the sixth fraction. The tenth fraction, which preferably is a bottoms fraction, contains a majority of the propane, if any, that was present in the sixth fraction. More preferably, the tenth fraction comprises at least about 60 weight percent, more preferably at least about 75 weight percent, and most preferably at least about 90 weight percent of the propane, if any, that was present in the sixth fraction. The fifth separation unit preferably includes one or more distillation and/or fractionation columns, absorbers and/or extractive distillation columns that are designed to form one or more overhead streams comprising polymerization grade propylene, and one or more bottoms streams comprising propane, if any was present in the sixth fraction.

In another embodiment, the fifth separation unit functions as a propane purge tower rather than a C3 splitter. In this embodiment, the propane purge tower operates in a similar manner as the C3 splitter, discussed above, although the propane purge tower includes fewer trays than a C3 splitter thereby providing a commensurate decrease in height and start-up costs. As a propane purge tower, the fifth separation unit preferably is a distillation column adapted to separate some of the propane from the sixth fraction. Specifically, the fifth separation unit separates the sixth fraction into a ninth fraction, which contains a majority of the propylene and some of the propane that was present in the sixth fraction, and a tenth fraction, which preferably contains some of the propane and optionally any residual C4+ components that were present in the sixth fraction. Ideally, the ninth fraction contains at least about 60 weight percent, more preferably at least about 75 weight percent, and most preferably at least about 90 weight percent of the propylene that was present in the sixth fraction. The ninth fraction also preferably contains less than about 10.0 weight percent, more preferably less than about 5.0 weight percent, and most preferably less than about 0.1 weight percent of the propane that was present in the sixth fraction. The tenth fraction preferably contains at least about 50 weight percent, more preferably at least about 80 weight percent, and most preferably at least about 90 weight percent of the propane that was present in the sixth fraction. Because propane is unreactive in most polymerization units, the ninth fraction is suitable for polymerization. The tenth fraction optionally is burned as fuel.

As discussed above, DME is particularly difficult to remove from the initial effluent stream. One preferred embodiment includes removing DME from the initial effluent stream in a plurality of steps (preferably in two steps). In this embodiment, the first separation unit, described above, removes a first portion of DME from the initial effluent stream in the second fraction. A second portion of the DME from the initial effluent stream remains in the first fraction. Thus, both the first and second fractions contain a detectable amount of DME. In terms of lower range limitations, the first fraction may include at least about 5 weight percent, more preferably at least about 10 weight percent, more preferably at least about 20 weight percent, and most preferably at least about 60 weight percent of the DME that was present in the initial effluent stream. The second fraction may include at least about 5 weight percent, more preferably at least about 10 weight percent, more preferably at least about 20 weight percent, and most preferably at least about 30 weight percent of the DME that was present in the initial effluent stream. The DME that remains in the first fraction then passes through the second separation unit, and the third separation unit and into the fifth separation unit via the fourth and sixth fractions. The fifth separation unit then separates the sixth fraction into a ninth fraction containing a majority of the propylene that was present in the fourth fraction, and a tenth fraction containing a majority of the propane and DME that was present in the fourth fraction. Thus, the first separation unit and the fifth separation unit act to remove DME. In one embodiment, the second fraction contains from about 10 weight percent to about 40 weight percent, more preferably from about 15 to about 35 weight percent, and most preferably from about 20 to about 30 weight percent of the DME that was present in the initial effluent stream. The tenth fraction from the fifth separation unit preferably contains from about 60 weight percent to about 90 weight percent, more preferably from about 65 to about 85 weight percent, and most preferably from about 70 to about 80 weight percent of the DME that was present in the initial effluent stream.

In this embodiment of the present invention, the one or more hydrogenation converters may be oriented in a variety of locations, although the converters ideally are oriented along one or more streams that contain acetylene. In the separation sequence described above, the one or more hydrogenation converters preferably receives and processes multiply unsaturated species from the first fraction, the fourth fraction, and/or from the fifth fraction, as these fractions contain the highest concentrations of acetylene.

Figure 2:
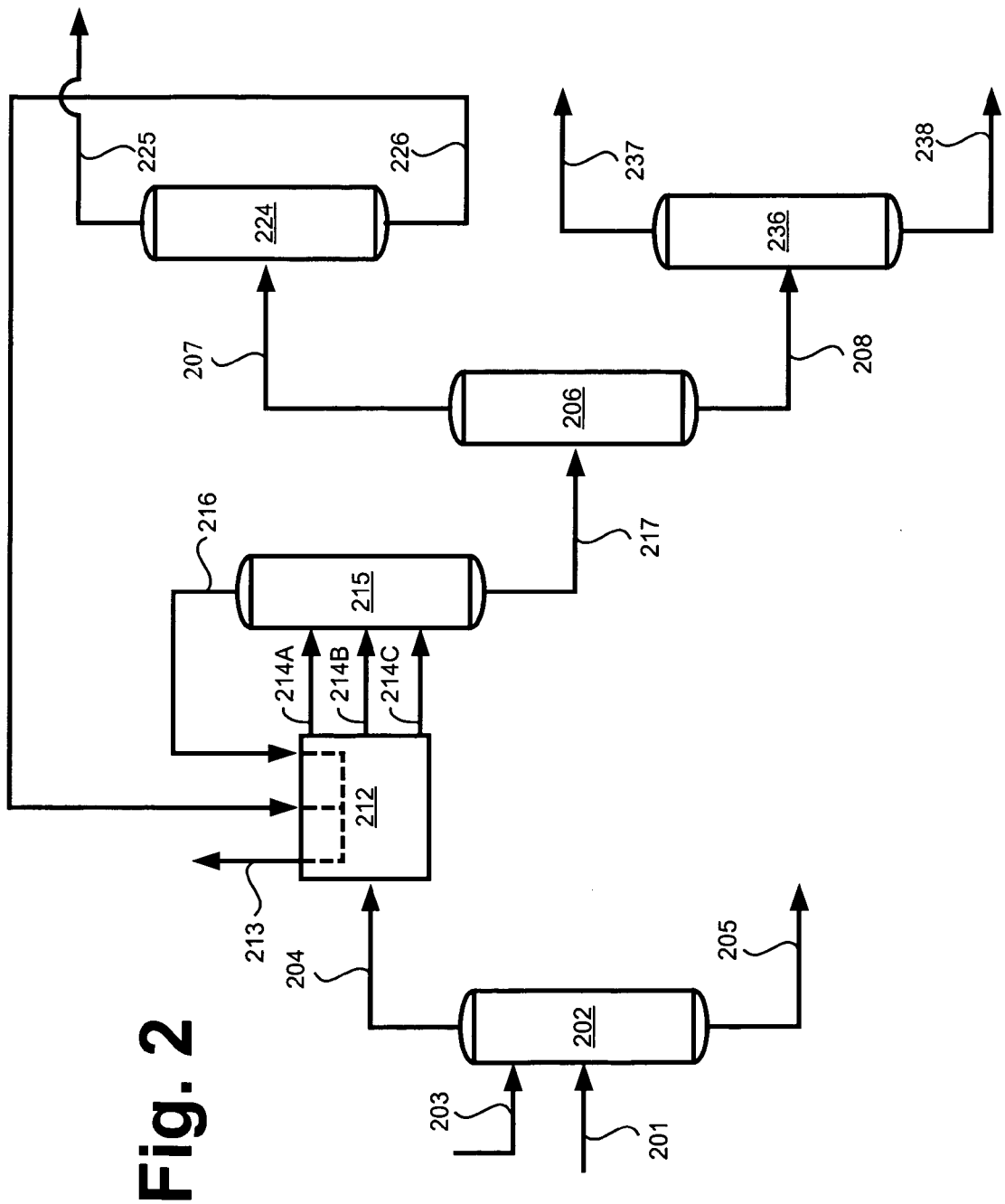
FIG. 2 illustrates a separation scheme according to another embodiment of the present invention.

FIG. 2 illustrates this embodiment of the present invention. As shown, initial effluent stream 201, which contains ethane, ethylene, DME, propane, and propylene is directed to first separation unit 202, which preferably is a distillation column adapted to separate ethylene and propylene and lighter components from the DME and heavier components, including any $C_4$+ components, and methanol. Additional methanol optionally is added to the first separation unit 202 though line 203 to reduce hydrate and/or free water formation in the first separation unit 202. The first separation unit 202 optionally includes a reflux and/or a reboiler line, not shown, to facilitate separation of these components. Specifically, the first separation unit 202 separates the initial effluent stream 201 into a first fraction 204, which contains a majority of the ethane, ethylene, propane and propylene that was present in the initial effluent stream 201, and a second fraction 205, which preferably contains a majority of the DME that was present in the initial effluent stream 201. The second fraction 205 also preferably contains a majority of the C4+ components and methanol, if any, that was present in the initial effluent stream 201.

Optionally, first fraction 204 is directed to a caustic wash unit to remove carbon dioxide, a water wash column, and/or a drying unit, not shown. Reverting to FIG. 2, the first fraction 204 is then directed to demethanizer feed train 212. Demethanizer feed train 212 is a "cold box" that preferably is formed of a series of coolers, e.g., Core Exchangers, and knock out drums, not shown, that cool the first fraction 204 and form a plurality of cooled streams 214A–C. Cooled streams 214A–C may be in liquid and/or vapor form. Preferably, cooled streams 214A–C are directed to a second separation unit 215 for further processing. The second separation unit 215 preferably is a distillation column adapted to separate light ends such as methane, hydrogen and/or carbon monoxide from ethane and ethylene. Specifically, the second separation unit 215 separates the cooled streams 214A–C, collectively, into a third fraction 216, which contains a majority of the light components that were present in the cooled streams 214A–C, and a fourth fraction 217, which preferably contains a majority of the ethane and ethylene that was present in the cooled streams 214A–C. The second separation unit 215 optionally includes a reflux and/or a reboiler line, not shown, to facilitate separation of the light components from ethane and ethylene. Third fraction 216 preferably is directed to the demethanizer feed train 212 for use as a cooling medium.

Fourth fraction 217 is directed to a third separation unit 206 for further processing. The third separation unit 206 preferably is a distillation column adapted to separate C2– components from C3+ components. Specifically, the second separation unit 206 separates the fourth fraction 217 into a fifth fraction 207, which contains a majority of the ethane and ethylene that was present in the fourth fraction 217, and a sixth fraction 208, which preferably contains a majority of the propane and propylene that was present in the fourth fraction 217. The third separation unit 206 optionally includes a reflux and/or a reboiler line, not shown, to facilitate separation of the C2– components from the C3+ components. Fifth fraction 207 is then introduced into a fourth separation unit 224 for further processing.

The fourth separation unit 224 preferably is a distillation column adapted to separate ethylene from ethane. Specifically, the fourth separation unit 224 separates the fifth fraction 207 into a seventh fraction 225, which contains a majority of the ethylene that was present in the fifth fraction 207, and an eighth fraction 226, which preferably contains a majority of the ethane that was present in the fifth fraction 207. The fourth separation unit 224 optionally includes a reflux line and/or a reboiler line, not shown, to facilitate separation of ethylene from ethane. Seventh fraction 225 contains relatively pure ethylene, which may be directed to a polymerization unit for polymerization. The eighth fraction 226 preferably is directed to the demethanizer feed train 212 for use as a cooling medium. Optionally, the eighth fraction 226 is combined with the cooling medium from third fraction 216, as shown by the broken line in demethanizer feed train 112. After cooling the vapor from first fraction 204 in the demethanizer feed train 212, the cooling mediums exit the demethanizer feed train 212 through tail gas line 213.

Sixth fraction 208 is well-suited for polymerization disposition, although the sixth fraction 208 may contain a minor amount of propane. If very high quality propylene is desired, then at least a portion of the sixth fraction 205 is introduced into a fifth separation unit 236. The fifth separation unit 236 preferably is a distillation column adapted to separate propylene from propane. The fifth separation unit 236 thus may operate as a C3 splitter. Specifically, the fifth separation unit 236 separates the sixth fraction 208 into a ninth fraction 237, which contains a majority of the propylene that was present in the sixth fraction 208, and a tenth fraction 238, which preferably contains a majority of the propane and optionally any residual C4+ components that were present in the sixth fraction 208. The fifth separation unit 236 optionally includes a reflux line and/or a reboiler line, not shown, to facilitate separation of propylene from the propane. The ninth fraction 237 contains very high quality propylene, which is suitable for polymerization. The tenth fraction 238 preferably is burned as fuel.

In another embodiment, the fifth separation unit 236 functions as a propane purge tower rather than a C3 splitter. The propane purge tower operates in a similar manner as the C3 splitter, discussed above, although the propane purge tower will include several fewer trays than a C3 splitter thereby providing a commensurate decrease in height and start-up costs. In this embodiment, the fifth separation unit 236 preferably is a distillation column adapted to separate some of the propane from the sixth fraction 208. Specifically, the fifth separation unit 236 separates the sixth fraction 208 into a ninth fraction 237, which contains a majority of the propylene and some of the propane that was present in the sixth fraction 208, and a tenth fraction 238, which preferably contains from about 1 to about 5 weight percent of the propane and optionally any residual C4+ components that were present in the sixth fraction 208. The fifth separation unit 236 in this embodiment also optionally includes a reflux line and/or a reboiler line and corresponding heat exchangers, not shown, to facilitate partial separation of propane from propylene. The ninth fraction 237 contains high quality propylene, which is suitable for polymerization. The tenth fraction 238 preferably is burned as fuel.

If the initial effluent stream 201 contains acetylene, methyl acetylene, propadiene, or other multiply unsaturated components, then the system of the present invention preferably includes a hydrogenation converter, e.g., an acetylene converter, not shown. If incorporated into the present invention, the hydrogenation converter preferably receives and processes one or more of the following streams: the first fraction 204, the fourth fraction 217, the fifth fraction 207, and/or the seventh fraction 225. In the hydrogenation converter, acetylene contacts hydrogen and carbon dioxide under conditions effective to convert at least a portion of the acetylene to ethylene. Similarly, methyl acetylene and/or propadiene contact hydrogen and carbon dioxide under conditions effective to convert at least a portion of the methyl acetylene and/or propadiene to propylene. Components other than acetylene, methyl acetylene and propadiene that are present in the above-identified streams preferably pass unaltered through the hydrogenation converter(s). The resulting acetylene-depleted streams are then processed as described above with reference to FIG. 2.

The MTO Reaction Process

As discussed above, the present invention is particularly suited for use with an effluent from an MTO reaction system, which is discussed in more detail hereinafter.

Typically, molecular sieve catalysts have been used to convert oxygenate compounds to light olefins. Silicoaluminophosphate (SAPO) molecular sieve catalysts are particularly desirable in such a conversion process, because they are highly selective in the formation of ethylene and propylene. A non-limiting list of preferable SAPO molecular sieve catalysts includes SAPO-17, SAPO-18, SAPO-34, SAPO-35, SAPO-44, the substituted forms thereof, and mixtures thereof.

The feedstock preferably contains one or more aliphatic-containing compounds that include alcohols, amines, carbonyl compounds for example aldehydes, ketones and carboxylic acids, ethers, halides, mercaptans, sulfides, and the like, and mixtures thereof. The aliphatic moiety of the aliphatic-containing compounds typically contains from 1 to about 50 carbon atoms, preferably from 1 to 20 carbon atoms, more preferably from 1 to 10 carbon atoms, and most preferably from 1 to 4 carbon atoms.

Non-limiting examples of aliphatic-containing compounds include: alcohols such as methanol and ethanol, alkyl-mercaptans such as methyl mercaptan and ethyl mercaptan, alkyl-sulfides such as methyl sulfide, alkyl-amines such as methyl amine, alkyl-ethers such as DME, diethyl ether and methylethyl ether, alkyl-halides such as methyl chloride and ethyl chloride, alkyl ketones such as dimethyl ketone, alkyl-aldehydes such as formaldehyde and acetaldehyde, and various acids such as acetic acid.

In a preferred embodiment of the process of the invention, the feedstock contains one or more oxygenates, more specifically, one or more organic compound(s) containing at least one oxygen atom. In the most preferred embodiment of the process of invention, the oxygenate in the feedstock is one or more alcohol(s), preferably aliphatic alcohol(s) where the aliphatic moiety of the alcohol(s) has from 1 to 20 carbon atoms, preferably from 1 to 10 carbon atoms, and most preferably from 1 to 4 carbon atoms. The alcohols useful as feedstock in the process of the invention include lower straight and branched chain aliphatic alcohols and their unsaturated counterparts. Non-limiting examples of oxygenates include methanol, ethanol, n-propanol, isopropanol, methyl ethyl ether, DME, diethyl ether, di-isopropyl ether, formaldehyde, dimethyl carbonate, dimethyl ketone, acetic acid, and mixtures thereof. In the most preferred embodiment, the feedstock is selected from one or more of methanol, ethanol, DME, diethyl ether or a combination thereof, more preferably methanol and DME, and most preferably methanol.

The various feedstocks discussed above, particularly a feedstock containing an oxygenate, more particularly a feedstock containing an alcohol, is converted primarily into one or more olefin(s). The olefin(s) or olefin monomer(s) produced from the feedstock typically have from 2 to 30 carbon atoms, preferably 2 to 8 carbon atoms, more preferably 2 to 6 carbon atoms, still more preferably 2 to 4 carbons atoms, and most preferably ethylene an/or propylene.

Non-limiting examples of olefin monomer(s) include ethylene, propylene, butene-1, pentene-1,4-methyl-pentene-1, hexene-1, octene-1 and decene-1, preferably ethylene, propylene, butene-1, pentene-1,4-methyl-pentene-1, hexene-1, octene-1 and isomers thereof. Other olefin monomer(s) include unsaturated monomers, diolefins having 4 to 18 carbon atoms, conjugated or nonconjugated dienes, polyenes, vinyl monomers and cyclic olefins.

In the most preferred embodiment, the feedstock, preferably of one or more oxygenates, is converted in the presence of a molecular sieve catalyst composition into olefin(s) having 2 to 6 carbons atoms, preferably 2 to 4 carbon atoms. Most preferably, the olefin(s), alone or combination, are converted from a feedstock containing an oxygenate, preferably an alcohol, most preferably methanol, to the preferred olefin(s) ethylene and/or propylene.

The most preferred process is generally referred to as gas-to-olefins (GTO) or alternatively, methanol-to-olefins (MTO). In an MTO process, a methanol containing feedstock, is converted in the presence of a molecular sieve catalyst composition into one or more olefins, preferably and predominantly, ethylene and/or propylene, often referred to as light olefins.

The feedstock, in one embodiment, contains one or more diluents, typically used to reduce the concentration of the feedstock. The diluents are generally non-reactive to the feedstock or molecular sieve catalyst composition. Non-limiting examples of diluents include helium, argon, nitrogen, carbon monoxide, carbon dioxide, water, essentially non-reactive paraffins (especially alkanes such as methane, ethane, and propane), essentially non-reactive aromatic compounds, and mixtures thereof. The most preferred diluents are water and nitrogen, with water being particularly preferred. In other embodiments, the feedstock does not contain any diluent.

The diluent may be used either in a liquid or a vapor form, or a combination thereof. The diluent is either added directly to a feedstock entering into a reactor or added directly into a reactor, or added with a molecular sieve catalyst composition. In one embodiment, the amount of diluent in the feedstock is in the range of from about 1 to about 99 mole percent based on the total number of moles of the feedstock and diluent, preferably from about 1 to 80 mole percent, more preferably from about 5 to about 50, most preferably from about 5 to about 25. In one embodiment, other hydrocarbons are added to a feedstock either directly or indirectly, and include olefin(s), paraffin(s), aromatic(s) (see for example U.S. Pat. No. 4,677,242, addition of aromatics) or mixtures thereof, preferably propylene, butylene, pentylene, and other hydrocarbons having 4 or more carbon atoms, or mixtures thereof.

The process for converting a feedstock, especially a feedstock containing one or more oxygenates, in the presence of a molecular sieve catalyst composition of the invention, is carried out in a reaction process in a reactor, where the process is a fixed bed process, a fluidized bed process (includes a turbulent bed process), preferably a continuous fluidized bed process, and most preferably a continuous high velocity fluidized bed process.

The reaction processes can take place in a variety of catalytic reactors such as hybrid reactors that have a dense bed or fixed bed reaction zones and/or fast fluidized bed reaction zones coupled together, circulating fluidized bed reactors, riser reactors, and the like. Suitable conventional reactor types are described in for example U.S. Pat. Nos. 4,076,796, 6,287,522 (dual riser), and Fluidization Engineering, D. Kunii and O. Levenspiel, Robert E. Krieger Publishing Company, New York, N.Y. 1977, which are all herein fully incorporated by reference.

The preferred reactor type are riser reactors generally described in Riser Reactor, Fluidization and Fluid-Particle Systems, pages 48 to 59, F. A. Zenz and D. F. Othmer, Reinhold Publishing Corporation, New York, 1960, and U.S. Pat. No. 6,166,282 (fast-fluidized bed reactor), and U.S. patent application Ser. No. 09/564,613 filed May 4, 2000 (multiple riser reactor), which are all herein fully incorporated by reference.

In an embodiment, the amount of liquid feedstock fed separately or jointly with a vapor feedstock, to a reactor system is in the range of from 0.1 weight percent to about 85 weight percent, preferably from about 1 weight percent to about 75 weight percent, more preferably from about 5 weight percent to about 65 weight percent based on the total weight of the feedstock including any diluent contained therein. The liquid and vapor feedstocks are preferably the same composition, or contain varying proportions of the same or different feedstock with the same or different diluent.

The conversion temperature employed in the conversion process, specifically within the reactor system, is in the range of from about 392° F. (200° C.) to about 1832° F. (1000° C.), preferably from about 482° F. (250° C.) to about 1472° F. (800° C.), more preferably from about 482° F. (250° C.) to about 1382° F. (750° C.), yet more preferably from about 572° F. (300° C.) to about 1202° F. (650° C.), yet even more preferably from about 662° F. (350° C.) to about 1112° F. (600° C.) most preferably from about 662° F. (350° C.) to about 1022° F. (550° C.).

The conversion pressure employed in the conversion process, specifically within the reactor system, varies over a wide range including autogenous pressure. The conversion pressure is based on the partial pressure of the feedstock exclusive of any diluent therein. Typically the conversion pressure employed in the process is in the range of from about 0.1 kPaa to about 5 MPaa, preferably from about 5 kPaa to about 1 MPaa, and most preferably from about 20 kPaa to about 500 kPaa.

The weight hourly space velocity (WHSV), particularly in a process for converting a feedstock containing one or more oxygenates in the presence of a molecular sieve catalyst composition within a reaction zone, is defined as the total weight of the feedstock excluding any diluents to the reaction zone per hour per weight of molecular sieve in the molecular sieve catalyst composition in the reaction zone. The WHSV is maintained at a level sufficient to keep the catalyst composition in a fluidized state within a reactor.

Typically, the WHSV ranges from about 1 $hr^{-1}$ to about 5000 $hr^{-1}$, preferably from about 2 $hr^{-1}$ to about 3000 $hr^{-1}$, more preferably from about 5 $hr^{-1}$ to about 1500 $hr^{-1}$, and most preferably from about 10 $hr^{-1}$ to about 1000 $hr^{-1}$. In one preferred embodiment, the WHSV is greater than 20 $hr^{-1}$, preferably the WHSV for conversion of a feedstock containing methanol, DME, or both, is in the range of from about 20 $hr^{-1}$ to about 300 $hr^{-1}$.

The superficial gas velocity (SGV) of the feedstock including diluent and reaction products within the reactor system is preferably sufficient to fluidize the molecular sieve catalyst composition within a reaction zone in the reactor. The SGV in the process, particularly within the reactor system, more particularly within the riser reactor(s), is at least about 0.1 meter per second (m/sec), preferably greater than 0.5 m/sec, more preferably greater than 1 m/sec, even more preferably greater than 2 m/sec, yet even more preferably greater than 3 m/sec, and most preferably greater than 4 m/sec. See for example U.S. patent application Ser. No. 09/708,753 filed Nov. 8, 2000, which is herein incorporated by reference.

Forming the Initial Effluent Stream from an MTO Reaction System

As indicated above, an MTO reaction system produces a product effluent stream which includes a minor amount of C4+ components (olefin and aliphatic) in addition to ethane, ethylene, propane and propylene. The product effluent also may include one or more of DME, hydrogen, methane, carbon monoxide, carbon dioxide, acetylene, methyl acetylene and propadiene. One non-limiting system for forming the initial effluent stream is discussed in more detail below.

Figure 3:
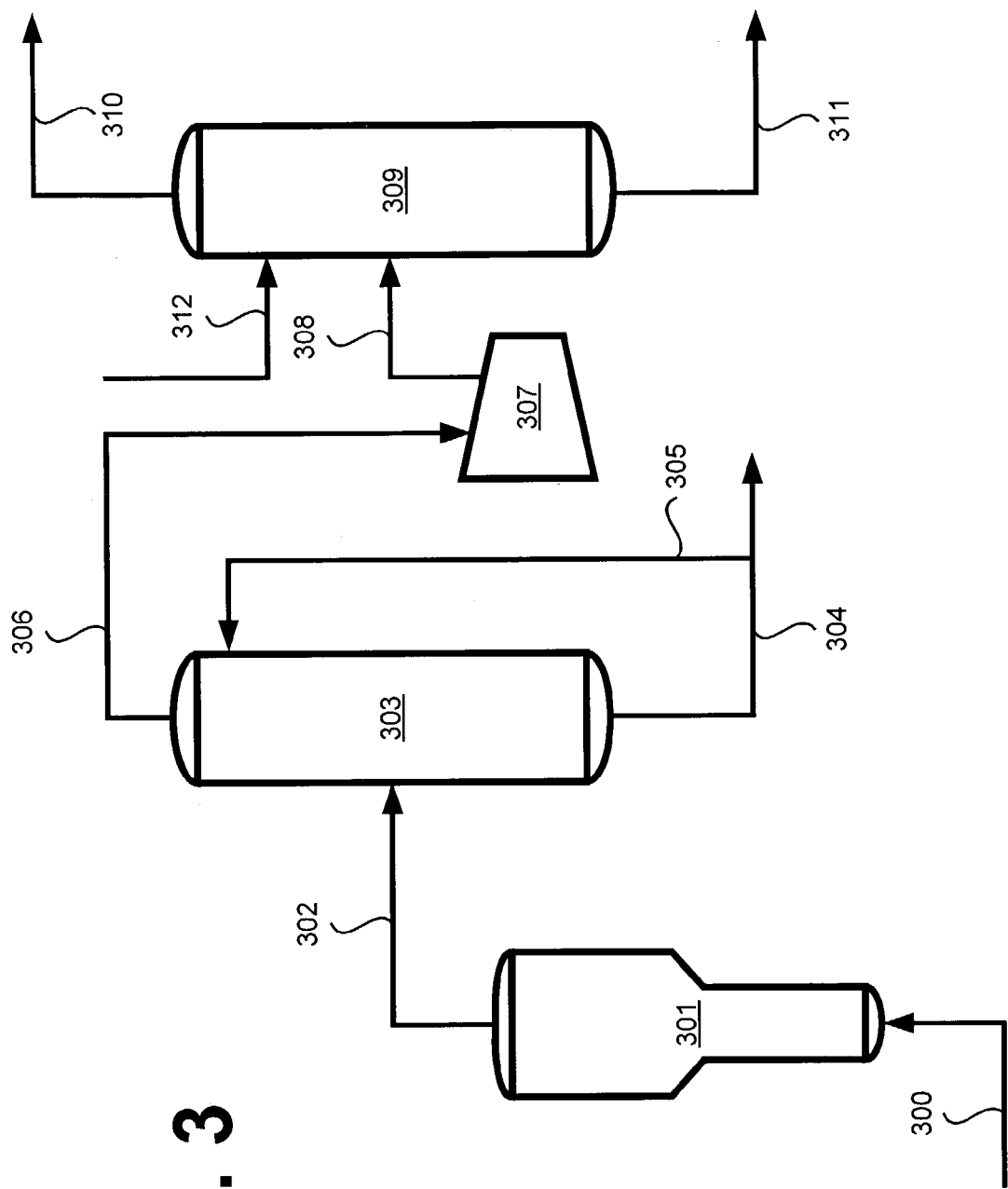
FIG. 3 illustrates an MTO reaction unit and an initial processing scheme.

One example illustrating how an initial effluent stream may be derived from an oxygenate to olefin reaction system, preferably from an MTO reaction system, is provided in FIG. 3. This example demonstrates one way of obtaining a stream containing ethane, ethylene, DME and propylene, and optionally C4+ components. In FIG. 3, methanol is sent through line 300 to an MTO reactor 301 wherein the methanol is converted to an olefin-containing stream 302 comprising methane, ethylene, ethane, propylene, propane, DME, and C4+ components, water and other hydrocarbon components. The olefin-containing stream 302 is directed to a quench tower 303 wherein the olefin-containing stream 302 is cooled and water and other condensable components are condensed.

The condensed components, which comprise a substantial amount of water, are withdrawn from the quench tower 303 through a bottoms line 304. A portion of the condensed components are circulated through line 305 back to the top of the quench tower 304. The line 305 contains a cooling unit, e.g., heat exchanger, not shown, to further cool the condensed components so as to provide a cooling medium to further cool the components in quench tower 304.

Olefin-containing vapor leaves through the overhead portion of quench tower 303 through line 306. The olefin-containing vapor is compressed in one or more compressors 307 to form a compressed stream 308. The compressed stream 308 optionally passes to a water absorption unit 309, where methanol, shown entering the water absorption unit 309 via line 312, is preferably used as the water absorbent. Olefins are recovered through overhead line 310. The overhead line 310 optionally contains ethane, ethylene, DME, propane, propylene, and C4+ hydrocarbons and may be processed as the "initial effluent stream" according to the present invention. That is, overhead line 310 optionally is directed to the first separation unit 102/202 and processed as shown in FIG. 1 and FIG. 2.

Ethylene and Propylene Disposition

The ethylene and propylene streams treated and separated according to this invention can be polymerized to form plastic compositions, e.g., polyolefins, particularly polyethylene and polypropylene. Any conventional process for forming polyethylene or polypropylene can be used. Catalytic processes are preferred. Particularly preferred are metallocene, Ziegler/Natta, aluminum oxide and acid catalytic systems. See, for example, U.S. Pat. Nos. 3,258,455; 3,305, 538; 3,364,190; 5,892,079; 4,659,685; 4,076,698; 3,645, 992; 4,302,565; and 4,243,691, the catalyst and process descriptions of each being expressly incorporated herein by reference. In general, these methods involve contacting the ethylene or propylene product with a polyolefin-forming catalyst at a pressure and temperature effective to form the polyolefin product.

In one embodiment of this invention, the ethylene or propylene product is contacted with a metallocene catalyst to form a polyolefin. Desirably, the polyolefin forming process is carried out at a temperature ranging between about 50° C. and about 320° C. The reaction can be carried out at low, medium or high pressure, being anywhere within the range of about 1 bar to about 3200 bar. For processes carried out in solution, an inert diluent can be used. In this type of operation, it is desirable that the pressure be at a range of from about 10 bar to about 150 bar, and preferably at a temperature range of from about 120° C. to about 250° C. For gas phase processes, it is preferred that the temperature generally be within a range of about 60° C. to 120° C., and that the operating pressure be from about 5 bar to about 50 bar.

In addition to polyolefins, numerous other olefin derivatives can be formed from the ethylene, propylene and C4+ olefins, particularly butylene, separated according to this invention. The olefins separated according to this invention can also be used in the manufacture of such compounds as aldehydes, acids such as $C_2$–$C_{13}$ mono carboxylic acids, alcohols such as $C_2$–$C_{12}$ mono alcohols, esters made from the $C_2$–$C_{12}$ mono carboxylic acids and the $C_2$–$C_{12}$ mono alcohols, linear alpha olefins, vinyl acetate, ethylene dicholoride and vinyl choride, ethylbenzene, ethylene oxide, cumene, acrolein, allyl chloride, propylene oxide, acrylic acid, ethylene-propylene rubbers, and acrylonitrile, and trimers and dimers of ethylene and propylene. The C4+ olefins, butylene in particular, are particularly suited for the manufacture of aldehydes, acids, alcohols, esters made from $C_5$–$C_{13}$ mono carboxylic acids and $C_5$–$C_{13}$ mono alcohols and linear alpha olefins.

Having now fully described the invention, it will be appreciated by those stilled in the art that the invention may be performed within a wide range of parameters within what is claimed, without departing from the spirit and scope of the invention.

The invention claimed is:

1. A process for separating components from an olefin-containing effluent stream, the process comprising the steps of:
   (a) providing the effluent stream, wherein the effluent stream contains ethane, ethylene, propylene, and dimethyl ether;
   (b) separating the effluent stream in a first separation unit into a first fraction and a second fraction, wherein the first fraction contains a majority of the ethane, ethylene and propylene present in the effluent stream, and wherein the second fraction contains a majority of the dimethyl ether present in the effluent stream;
   (c) separating at least a portion of the first fraction into a third fraction and a fourth fraction, wherein the third fraction contains a majority of the ethylene and ethane present in the at least a portion of the first fraction, and wherein the fourth fraction contains a majority of the propylene present in the at least a portion of the first fraction, wherein the effluent stream, the first fraction, and the third fraction further contain methane and acetylene;
   (d) separating at least a portion of the third fraction into a fifth fraction and a sixth fraction, wherein the fifth fraction contains a majority of the methane present in the at least a portion of the third fraction; and the sixth fraction contains a majority of the acetylene, ethylene and ethane present in the at least a portion of the third fraction; and
   (e) contacting the acetylene in at least a portion of the sixth fraction, or in a portion separated from the sixth fraction, with hydrogen and carbon monoxide under conditions effective to convert at least a portion of the acetylene to ethylene.

2. The process of claim 1, the process further comprising the step of contacting the acetylene in the at least a portion of the sixth fraction with hydrogen and carbon monoxide under conditions effective to convert at least a portion of the acetylene to ethylene, thereby forming an acetylene-depleted stream comprising ethylene and ethane.

3. The process of claim 2, wherein the process further comprises the step of separating at least a portion of the acetylene-depleted stream into a seventh fraction and an eighth fraction, wherein the seventh fraction contains a majority of the ethylene present in the at least a portion of the acetylene-depleted stream, and wherein the eighth fraction contains a majority of the ethane present in the at least a portion of the acetylene-depleted stream.

4. The process of claim 1 wherein the process further comprises the step of separating at least a portion of the sixth fraction into a seventh fraction and an eighth fraction, wherein the seventh fraction contains a majority of the ethylene present in the at least a portion of the sixth fraction, and wherein the eighth fraction contains a majority of the ethane present in the at least a portion of sixth fraction.

5. The process of claim 4, wherein the effluent stream, the first fraction and the fourth fraction further contain propane, the process further comprising the step of separating at least a portion of the fourth fraction into a ninth fraction and a tenth fraction, wherein the ninth fraction contains a majority of the propylene present in the at least a portion of the fourth fraction, and wherein the tenth fraction contains a majority of the propane present in the at least a portion of the fourth fraction.

6. The process of claim 1, wherein the effluent stream, the first fraction and the fourth fraction further contain propane, the process further comprising the step of separating at least a portion of the fourth fraction into a ninth fraction and a tenth fraction, wherein the ninth fraction contains a majority of the propylene present in the at least a portion of the fourth fraction, and wherein the tenth fraction contains a majority of the propane present in the at least a portion of the fourth fraction.

7. The process of claim 6, wherein at least a portion of the tenth fraction is recycled to the first separation unit.

8. The process of claim 1, wherein the effluent stream and the first fraction further contain carbon dioxide, the process further comprising the step of contacting the first fraction with a caustic medium under conditions effective to remove carbon dioxide from the first fraction.

9. The process of claim 1, wherein step (b) occurs at a pressure of at least 200 psig.

10. The process of claim 9, wherein the pressure is from 200 to 290 psig.

11. The process of claim 10, wherein the pressure is from 250 to 290 psig.

12. The process of claim 1, wherein the effluent stream further contains water in an amount not greater than 15,000 wppm.

13. The process of claim 12, wherein the water is present in an amount of from 10 to 15,000 wppm.

14. The process of claim 1, wherein the effluent stream further contains at least 500 wppm dimethyl ether.

15. The process of claim 1, wherein the effluent stream contains not greater than 50 weight percent dimethyl ether.

16. The process of claim 1, wherein the effluent stream further contains propane, and wherein the first fraction contains a majority of the propane present in the effluent stream.

17. The process of claim 1, wherein the effluent stream further contains propane, and wherein the second fraction contains a majority of the propane present in the effluent stream.

18. The process of claim 1, wherein the first fraction contains not greater than 100 wppm dimethyl ether.

19. The process of claim 1, wherein the first separation unit comprises a distillation column.

20. The process of claim 19, wherein a water absorbent is added to the distillation column.

21. The process of claim 20, wherein the water absorbent is added to the distillation column at a molar ratio or water absorbent to total effluent stream to be separated of from 4:1 to 1:5,000.

22. The process of claim 1, wherein the effluent stream contains from 50 to 95 combined weight percent ethylene and propylene, based on the total weight of the effluent stream.

23. The process of claim 1, wherein the effluent stream contains from 25 to 75 weight percent ethylene, based on the total weight of the effluent stream.

24. The process of claim 1, wherein the effluent stream contains from 25 to 75 weight percent propylene, based on the total weight of the effluent stream.

25. The process of claim 1, wherein the effluent stream further contains $CO_2$, and the first fraction further contains at least a majority of the $CO_2$ present in the effluent stream.

26. The process of claim 25, wherein the process further comprises the step of acid gas treating the first fraction.

27. The process of claim 1, wherein the effluent stream further contains C$_4$+ hydrocarbon components, and the second fraction further contains at least a majority of the C$_4$+ hydrocarbon components present in the effluent stream.

28. The process of claim 3, wherein the process further comprises the step of polymerizing the ethylene from the seventh fraction.

29. The process of claim 6, wherein the process further comprises the step of polymerizing the propylene from the ninth fraction.

30. The process of claim 20, wherein the process further comprises the step contacting the first fraction with water, acid gas treating the water contacted first fraction, and drying the acid gas treated first fraction.

31. The process of claim 1, wherein step (b) occurs at a pressure of less than 200 psig.

32. The process of claim 31, wherein the pressure is from 100 to 200 psig.

33. The process of claim 32, wherein the pressure is from 120 to 180 psig.

34. The process of claim 31, wherein the first separation unit comprises a distillation column.

35. The process of claim 34, wherein a water absorbent is added to the distillation column.

36. The process of claim 35, wherein the second fraction has an average temperature of not greater than 210° F.

37. A process for separating components from an olefin-containing effluent stream, the process comprising the steps of:
(a) providing the effluent stream, wherein the effluent stream contains methane, ethane, ethylene, propane, propylene, and dimethyl ether;
(b) separating the effluent stream in a first separation unit into a first fraction and a second fraction, wherein the first fraction contains a majority of the methane, ethane, ethylene, propane and propylene present in the effluent stream, and wherein the second fraction contains a majority of the dimethyl ether present in the effluent stream;
(c) separating at least a portion of the first fraction into a third fraction and a fourth fraction, wherein the third fraction contains a majority of the methane that was present in the at least a portion of the first fraction, and wherein the fourth fraction contains a majority of the ethylene, ethane, propylene and propane that was present in the at least a portion of the first fraction, wherein the effluent stream, the first fraction, and the fourth fraction further contain acetylene; and
(d) contacting acetylene in the fourth fraction, or in an acetylene-containing fraction separated from the fourth fraction, with hydrogen and carbon monoxide under conditions effective to convert at least a portion of the acetylene to ethylene.

38. The process of claim 37, wherein the process further comprises the step of separating at least a portion of the fourth fraction into a fifth fraction and a sixth fraction, wherein the fifth fraction contains a majority of the ethylene and ethane that was present in the at least a portion of the fourth fraction, and wherein the sixth fraction contains majority of the propylene and propane that was present in the at least a portion of the fourth fraction.

39. The process of claim 38, wherein the fifth fraction contains acetylene, and wherein the process comprises the step of contacting the acetylene in at least a portion of the fifth fraction with hydrogen and carbon monoxide under conditions effective to convert at least a portion of the acetylene to ethylene, thereby forming an acetylene-depleted stream comprising ethylene and ethane.

40. The process of claim 39, wherein the process further comprises the step of separating at least a portion of the acetylene-depleted stream into a seventh fraction and an eighth fraction, wherein the seventh fraction contains a majority of the ethylene present in the at least a portion of the acetylene-depleted stream, and wherein the eighth fraction contains a majority of the ethane present in the at least a portion of acetylene-depleted stream.

41. The process of claim 40, the process further comprising the step of separating at least a portion of the sixth fraction into a ninth fraction and a tenth fraction, wherein the ninth fraction contains a majority of the propylene present in the at least a portion of the sixth fraction, and wherein the tenth fraction contains a majority of the propane present in the at least a portion of the sixth fraction.

42. The process of claim 41, wherein at least a portion of the tenth fraction is recycled to the first separation unit.

43. The process of claim 38, wherein the process further comprises the step of separating at least a portion of the fifth fraction into a seventh fraction and an eighth fraction, wherein the seventh fraction contains a majority of the ethylene present in the at least a portion of the fifth fraction, and wherein the eighth fraction contains a majority of the ethane present in the at least a portion of fifth fraction.

44. The process of claim 43, the process further comprising the step of separating at least a portion of the sixth fraction into a ninth fraction and a tenth fraction, wherein the ninth fraction contains a majority of the propylene present in the at least a portion of the sixth fraction, and wherein the tenth fraction contains a majority of the propane present in the at least a portion of the sixth fraction.

45. The process of claim 38, the process further comprising the step of separating at least a portion of the sixth fraction into a ninth fraction and a tenth fraction, wherein the ninth fraction contains a majority of the propylene present in the at least a portion of the sixth fraction, and wherein the tenth fraction contains a majority of the propane present in the at least a portion of the sixth fraction.

46. The process of claim 45, wherein at least a portion of the tenth fraction is recycled to the first separation unit.

47. The process of claim 37, wherein the effluent stream and the first fraction further contain carbon dioxide, the process further comprising the step of contacting the first fraction with a caustic medium under conditions effective to remove carbon dioxide from the first fraction.

48. The process of claim 37, wherein step (b) occurs at a pressure of at least 200 psig.

49. The process of claim 48, wherein the pressure is from 200 to 290 psig.

50. The process of claim 49, wherein the pressure is from 250 to 290 psig.

51. The process of claim 37, wherein the effluent stream further contains water in an amount not greater than 15,000 wppm.

52. The process of claim 51, wherein the water is present in an amount of from 10 to 15,000 wppm.

53. The process of claim 37, wherein the effluent stream further contains at least 500 wppm dimethyl ether.

54. The process of claim 37, wherein the effluent stream contains not greater than 50 weight percent dimethyl ether.

55. The process of claim 37, wherein the first fraction contains not greater than 100 wppm dimethyl ether.

56. The process of claim 37, wherein the first separation unit comprises a distillation column.

57. The process of claim 56, wherein a water absorbent is added to the distillation column.

58. The process of claim 57, wherein the water absorbent is added to the distillation column at a molar ratio of water absorbent to total effluent steam to be separated of from 4:1 to 1:5,000.

59. The process of claim 37, wherein the effluent stream contains from 50 to 95 combined weight percent ethylene and propylene, based on the total weight of the effluent stream.

60. The process of claim 37, wherein the effluent stream contains from 25 to 75 weight percent ethylene, based on the total weight of the effluent stream.

61. The process of claim 37, wherein the effluent stream contains from 25 to 75 weight percent propylene, based on the total weight of the effluent stream.

62. The process of claim 37, wherein the effluent stream further contains $CO_2$, and the first fraction further contains at least a majority of the $CO_2$ in the effluent stream.

63. The process of claim 62, wherein the process further comprises the step of acid gas treating the first fraction.

64. The process of claim 37, wherein the effluent stream further contains $C_4+$ hydrocarbon components, and the second fraction further contains at least a majority of the $C_4+$ hydrocarbon components present in the effluent stream.

65. The process of claim 40, wherein the process further comprises the step of polymerizing the ethylene from the seventh fraction.

66. The process of claim 45, wherein the process further comprises the step of polymerizing the propylene from the ninth fraction.

67. The process of claim 50, wherein the process further comprises the step of contacting the first fraction with water, acid gas treating the water contacted first fraction, and drying the acid gas treated first fraction.

68. The process of claim 37, wherein step (b) occurs at a pressure of less than 200 psig.

69. The process of claim 68, wherein the pressure is from 100 to 200 psig.

70. The process of claim 69, wherein the pressure is from 120 to 180 psig.

71. The process of claim 68, wherein the first separation unit comprises a distillation column.

72. The process of claim 71, wherein a water absorbent is added to the distillation column.

73. The process of claim 72, wherein the second fraction has an average temperature of not greater than 210° F.

74. The process of claim 44, wherein at least a portion of the tenth fraction is recycled to the first separation unit.

75. A process for selectively hydrogenating acetylene, the process comprising the steps of:
  (a) providing an effluent stream containing methane, acetylene, ethylene, ethane, propylene, propane and dimethyl ether;
  (b) separating the effluent stream in a first separation unit into a first fraction and a second fraction, wherein the first fraction contains a first portion of the propane and a majority of the methane, ethane, ethylene and propylene present in the effluent stream, and wherein the second fraction contains a second portion of the propane and a majority of the dimethyl ether present in the effluent stream;
  (c) separating at least a portion of the first fraction into a third fraction and a fourth fraction, wherein the third fraction contains a majority of the methane, ethylene and ethane present in the at least a portion of the first fraction, and wherein the fourth fraction contains a majority of the propylene and propane present in the at least a portion of the first fraction;
  (d) separating at least a portion of the third fraction into a fifth fraction and a sixth fraction, wherein the fifth fraction contains a majority of the methane present in the at least a portion of the third fraction, and wherein the sixth fraction contains a majority of the ethylene and ethane present in the at least a portion of the third fraction;
  (e) separating at least a portion of the sixth fraction into a seventh fraction and an eight fraction, wherein the seventh fraction contains a majority of the ethylene present in the at least a portion of the sixth fraction, and wherein the eighth fraction contains a majority of the ethane present in the at least a portion of the sixth fraction; and
  (f) contacting acetylene in an acetylene-containing stream with hydrogen and carbon monoxide in a conversion unit under conditions effective to at least partially hydrogenate at least a portion of the acetylene in the acetylene-containing stream, wherein the acetylene-containing stream is selected from the group consisting of the sixth fraction and the seventh fraction.

76. The process of claim 75, wherein the acetylene-containing stream is the sixth fraction.

77. The process of claim 75, wherein the acetylene-containing stream is the seventh fraction.

78. A process for separating components from an olefin-containing effluent stream, the process comprising the steps of:
  (a) providing the effluent stream, wherein the effluent stream contains ethane, ethylene, dimethyl ether, and propylene;
  (b) separating the effluent stream into a first fraction and a second fraction, wherein the first fraction contains at least 5 weight percent of the dimethyl ether and a majority of the ethane, ethylene and propylene present in the effluent stream, and wherein the second fraction contains at least 5 weight percent of the dimethyl ether and a majority of the C4+ components present in the effluent stream; and
  (c) separating at least a portion of the first fraction into a third fraction and a fourth fraction, wherein the fourth fraction contains a majority of the dimethyl ether present in the at least a portion of the first fraction.

79. The process of claim 78, wherein the third fraction contains a majority of the ethylene and ethane that was present in the first fraction, and wherein the fourth fraction further contains a majority of the propylene that was present in the first fraction.

80. The process of claim 79, wherein the process further comprises the step of separating at least a portion of the fourth fraction into a ninth fraction and a tenth fraction, wherein the ninth fraction contains a majority of the propylene present in the at least a portion of the fourth fraction, and wherein the tenth fraction contains a majority of the dimethyl ether present in the at least a portion of the fourth fraction.

81. The process of claim 80, wherein the tenth fraction further contains a majority of the propane that was present in the at least a portion of the fourth fraction.

82. The process of claim 78, wherein the effluent stream, the first fraction and the third fraction further contains methane, the process further comprising the step of separating at least a portion of the fourth fraction into a fifth fraction and a sixth fraction, wherein the fifth fraction contains a majority of the methane present in the at least a portion of the fourth fraction, and wherein the fifth fraction contains a majority of the ethane and ethylene present in the at least a portion of the fourth fraction.

83. The process of claim 82, wherein the process further comprises the step of separating at least a portion of the sixth fraction into a seventh fraction and an eighth fraction, wherein the seventh fraction contains a majority of the ethylene present in the at least a portion of the sixth fraction, and wherein the eighth fraction contains a majority of the ethane present in the at least a portion of the sixth fraction.

84. The process of claim 78, wherein the first fraction contains at least 10 weight percent of the dimethyl ether present in the effluent stream.

85. The process of claim 84, wherein the first fraction contains at least 20 weight percent of the dimethyl ether present in the effluent stream.

86. The process of claim 85, wherein the first fraction contains at least 60 weight percent of the dimethyl ether present in the effluent stream.

87. The process of claim 78, wherein the second fraction contains at least 10 weight percent of the dimethyl ether present in the effluent stream.

88. The process of claim 87, wherein the second fraction contains at least 20 weight percent of the dimethyl ether present in the effluent stream.

89. The process of claim 88, wherein the second fraction contains at least 30 weight percent of the dimethyl ether present in the effluent stream.

90. The process of claim 78, wherein the effluent stream and the first fraction further comprise methane and the third fraction contains a majority of the methane present in the at least a portion of the first fraction, and wherein the fourth fraction further contains a majority of the ethane, ethylene and propylene present in the first fraction.

91. The process of claim 90, wherein the process further comprises the step of separating at least a portion of the fourth fraction into a fifth fraction and a sixth fraction, wherein the fifth fraction contains a majority of the ethane and ethylene present in the at least a portion of the fourth fraction, and wherein the fifth fraction contains a majority of the dimethyl ether and propylene present in the at least a portion of the fourth fraction.

92. The process of claim 91, wherein the process further comprises the step of separating at least a portion of the fifth fraction into a seventh fraction and an eighth fraction, wherein the seventh fraction contains a majority of the ethylene present in the at least a portion of the fifth fraction, and wherein the eighth fraction contains a majority of the ethane present in the at least a portion of the sixth fraction.

93. The process of claim 91, wherein the process further comprises the step of separating at least a portion of the sixth fraction into a ninth fraction and a tenth fraction, wherein the ninth fraction contains a majority of the propylene present in the at least a portion of the sixth fraction, and wherein the tenth fraction contains a majority of the dimethyl ether present in the at least a portion of the sixth fraction.

94. The process of claim 93, wherein the effluent stream, the first fraction, the forth fraction and the sixth fraction further contain propane and wherein the tenth fraction further contains a majority of the propane that was present in the at least a portion of the sixth fraction.

* * * * *